United States Patent
Singh et al.

(10) Patent No.: US 10,893,951 B2
(45) Date of Patent: Jan. 19, 2021

(54) DEVICE AND METHOD FOR CORRECTING SPINAL DEFORMITIES IN PATIENTS

(71) Applicant: Minimally Invasive Spinal Technology, LLC, Charlottesville, VA (US)

(72) Inventors: Alexander Singh, Virginia Beach, VA (US); Rohit Rustagi, Hillsborough, NJ (US); George Vithoulkas, Henrico, VA (US); Eric Taleghani, Yorktown, VA (US); Hasan Syed, Woodbridge, VA (US)

(73) Assignee: Minimally Invasive Spinal Technology, LLC, Charlottesville, VA (US)

( * ) Notice: Subject to any disclaimer, the term of this patent is extended or adjusted under 35 U.S.C. 154(b) by 0 days.

(21) Appl. No.: 16/535,007

(22) Filed: Aug. 7, 2019

(65) Prior Publication Data

US 2020/0046511 A1    Feb. 13, 2020

Related U.S. Application Data

(60) Provisional application No. 62/715,638, filed on Aug. 7, 2018.

(51) Int. Cl.
*A61F 2/44*    (2006.01)
*A61F 2/30*    (2006.01)

(52) U.S. Cl.
CPC .......... *A61F 2/442* (2013.01); *A61F 2/30749* (2013.01); *A61F 2/4425* (2013.01);
(Continued)

(58) Field of Classification Search
CPC .. A61F 2/44–447; A61F 2/442; A61F 2/4425; A61F 2002/448–4485; A61F 2002/30014; A61F 2002/30069
See application file for complete search history.

(56) References Cited

U.S. PATENT DOCUMENTS 3,867,728 A * 2/1975 Stubstad ............. A61F 2/30907
                                            623/17.16
4,309,777 A * 1/1982 Patil ....................... A61F 2/442
                                            606/247
(Continued)

FOREIGN PATENT DOCUMENTS

WO    2004016217 A2    2/2004

OTHER PUBLICATIONS

PCT Search Report and Written Opinion in Co-Pending PCT/US2019/045581 (10 pages).

*Primary Examiner* — Eduardo C Robert
*Assistant Examiner* — Michelle C Eckman
(74) *Attorney, Agent, or Firm* — Woods Rogers PLC; Nathan A. Evans

(57) ABSTRACT

Devices and related methods for the dynamic correction of spinal deformities are disclosed. The devices and methods are particularly useful for correcting an abnormal curvature of the spine. In one exemplary embodiment, a method for correcting deformity via a spinal implant that can include a polymer between or attached to a top and bottom plate, which can exist in a wedge-shaped configuration in order to apply asymmetric forces to the spinal column, is provided. The implant may be inserted between adjacent vertebrae comprising part of the abnormal curvature, thereby restoring the normal curvature of a spine.

18 Claims, 22 Drawing Sheets

(52) U.S. Cl.
CPC ............ *A61F 2002/30014* (2013.01); *A61F 2002/30069* (2013.01); *A61F 2002/30131* (2013.01); *A61F 2002/30133* (2013.01); *A61F 2002/30159* (2013.01); *A61F 2002/30326* (2013.01); *A61F 2002/30471* (2013.01); *A61F 2002/30841* (2013.01); *A61F 2002/30878* (2013.01)

(56) References Cited

U.S. PATENT DOCUMENTS

| | | | |
|---|---|---|---|
| 4,759,769 A * | 7/1988 | Hedman | A61F 2/4425 623/17.13 |
| 5,123,926 A * | 6/1992 | Pisharodi | A61F 2/441 606/247 |
| 5,320,644 A * | 6/1994 | Baumgartner | A61F 2/442 606/247 |
| 5,545,229 A * | 8/1996 | Parsons | A61F 2/442 623/17.15 |
| 5,676,702 A * | 10/1997 | Ratron | A61F 2/442 623/17.16 |
| 5,827,328 A * | 10/1998 | Buttermann | A61F 2/442 623/17.13 |
| 5,928,284 A * | 7/1999 | Mehdizadeh | A61F 2/441 606/247 |
| 6,045,579 A | 4/2000 | Hochshuler et al. | |
| 6,080,193 A | 6/2000 | Hochshuler et al. | |
| 6,231,609 B1 * | 5/2001 | Mehdizadeh | A61F 2/441 623/17.11 |
| 6,296,664 B1 * | 10/2001 | Middleton | A61F 2/30744 623/17.13 |
| 6,315,797 B1 * | 11/2001 | Middleton | A61F 2/30744 623/17.16 |
| 6,436,102 B1 | 8/2002 | Ralph et al. | |
| 6,447,548 B1 | 9/2002 | Ralph et al. | |
| 6,468,310 B1 * | 10/2002 | Ralph | A61F 2/4425 623/17.13 |
| 6,471,725 B1 | 10/2002 | Ralph et al. | |
| 6,520,996 B1 * | 2/2003 | Manasas | B22F 3/1055 623/23.5 |
| 6,527,804 B1 * | 3/2003 | Gauchet | A61F 2/442 623/17.12 |
| 6,562,047 B2 | 5/2003 | Ralph et al. | |
| 6,607,559 B2 | 8/2003 | Ralph et al. | |
| 6,682,564 B1 | 1/2004 | Duarte | |
| 6,733,532 B1 * | 5/2004 | Gauchet | A61F 2/442 606/247 |
| 6,740,119 B2 | 5/2004 | Ralph et al. | |
| 6,770,094 B2 * | 8/2004 | Fehling | A61F 2/30742 623/17.13 |
| 6,805,716 B2 | 10/2004 | Ralph et al. | |
| 6,837,904 B2 | 1/2005 | Ralph et al. | |
| 6,863,689 B2 | 3/2005 | Ralph et al. | |
| 6,890,356 B2 | 5/2005 | Ralph et al. | |
| 6,964,686 B2 * | 11/2005 | Gordon | A61F 2/442 623/17.14 |
| 7,153,310 B2 | 12/2006 | Ralph et al. | |
| 7,217,292 B2 | 5/2007 | Ralph et al. | |
| 7,331,994 B2 * | 2/2008 | Gordon | A61F 2/442 623/17.13 |
| 7,507,255 B2 | 3/2009 | Ralph et al. | |
| 7,550,008 B2 | 6/2009 | Ralph et al. | |
| 7,722,675 B2 | 5/2010 | Ralph et al. | |
| 7,731,753 B2 * | 6/2010 | Reo | A61B 17/7062 623/17.13 |
| 7,763,075 B2 * | 7/2010 | Navarro | A61F 2/442 623/17.11 |
| 7,780,733 B2 | 8/2010 | Carver et al. | |
| 7,922,767 B2 | 4/2011 | Sack et al. | |
| 8,038,717 B2 | 10/2011 | Ralph et al. | |
| 8,097,037 B2 | 1/2012 | Serhan et al. | |
| 8,118,873 B2 | 2/2012 | Humphreys et al. | |
| 8,172,902 B2 * | 5/2012 | Kapitan | A61F 2/442 623/17.14 |
| 8,216,315 B2 | 7/2012 | Ralph et al. | |
| 8,298,287 B2 * | 10/2012 | Moumene | A61F 2/442 623/17.16 |
| 8,313,529 B2 * | 11/2012 | Lechmann | A61F 2/4425 623/17.16 |
| 8,361,153 B2 | 1/2013 | Ralph et al. | |
| 8,366,776 B2 | 2/2013 | Heinz | |
| 8,377,138 B2 | 2/2013 | Reo et al. | |
| 8,382,838 B2 | 2/2013 | Baumgartner et al. | |
| 8,845,730 B2 * | 9/2014 | de Villiers | A61F 2/442 623/17.14 |
| 8,951,300 B2 * | 2/2015 | Parrish | A61F 2/442 623/17.11 |
| 9,034,045 B2 | 5/2015 | Davenport et al. | |
| 9,039,766 B1 * | 5/2015 | Fonte | A61F 2/442 623/17.11 |
| 9,060,876 B1 * | 6/2015 | To | A61F 2/442 |
| 9,237,958 B2 * | 1/2016 | Duggal | A61B 17/1604 |
| 9,687,354 B2 * | 6/2017 | Bellas | A61F 2/442 |
| 10,433,974 B2 * | 10/2019 | O'Neil | A61F 2/4455 |
| 2003/0083749 A1 * | 5/2003 | Kuslich | A61F 2/44 623/17.16 |
| 2004/0078080 A1 * | 4/2004 | Thramann | A61F 2/442 623/17.15 |
| 2005/0015150 A1 * | 1/2005 | Lee | A61F 2/441 623/17.12 |
| 2005/0027364 A1 * | 2/2005 | Kim | A61F 2/4425 623/17.13 |
| 2005/0112397 A1 * | 5/2005 | Rolfe | A61B 17/8605 428/593 |
| 2005/0113924 A1 * | 5/2005 | Buttermann | A61B 17/1671 623/17.13 |
| 2005/0251260 A1 * | 11/2005 | Gerber | A61F 2/441 623/17.13 |
| 2006/0085009 A1 * | 4/2006 | Truckai | A61B 17/7094 606/94 |
| 2006/0142861 A1 * | 6/2006 | Murray | A61F 2/442 623/17.13 |
| 2006/0149381 A1 * | 7/2006 | Kim | A61F 2/442 623/17.13 |
| 2006/0178744 A1 * | 8/2006 | de Villiers | A61F 2/4425 623/17.13 |
| 2006/0200239 A1 * | 9/2006 | Rothman | A61F 2/44 623/17.13 |
| 2006/0293753 A1 * | 12/2006 | Thramann | A61F 2/442 623/17.13 |
| 2007/0050032 A1 * | 3/2007 | Gittings | A61F 2/442 623/17.12 |
| 2007/0067037 A1 * | 3/2007 | Studer | A61F 2/4455 623/17.13 |
| 2007/0067038 A1 * | 3/2007 | Studer | A61F 2/4425 623/17.13 |
| 2007/0088441 A1 * | 4/2007 | Duggal | A61B 17/1604 623/17.16 |
| 2007/0168039 A1 * | 7/2007 | Trieu | A61B 17/7062 623/17.15 |
| 2007/0191958 A1 * | 8/2007 | Abdou | A61B 17/7035 623/17.16 |
| 2007/0270959 A1 * | 11/2007 | Dubousset | A61B 17/702 623/17.11 |
| 2008/0114454 A1 * | 5/2008 | Peterman | A61F 2/44 623/17.16 |
| 2008/0154375 A1 * | 6/2008 | Serhan | A61F 2/441 623/17.16 |
| 2008/0161919 A1 * | 7/2008 | Melkent | A61B 17/7062 623/17.11 |
| 2008/0161920 A1 * | 7/2008 | Melkent | A61B 17/7062 623/17.11 |
| 2008/0288074 A1 * | 11/2008 | O'Neil | A61F 2/442 623/17.16 |
| 2008/0312743 A1 * | 12/2008 | Vila | A61F 2/442 623/17.16 |
| 2009/0012623 A1 * | 1/2009 | Sack | A61F 2/442 623/17.16 |
| 2009/0132049 A1 | 5/2009 | Carver et al. | |

(56) References Cited

U.S. PATENT DOCUMENTS

| | | | |
|---|---|---|---|
| 2009/0157185 A1* | 6/2009 | Kim | A61F 2/442 623/17.16 |
| 2009/0192617 A1* | 7/2009 | Arramon | A61F 2/4425 623/17.16 |
| 2009/0292363 A1* | 11/2009 | Goldfarb | A61F 2/442 623/17.16 |
| 2010/0030335 A1* | 2/2010 | Arramon | A61F 2/36 623/17.13 |
| 2010/0286783 A1* | 11/2010 | Lechmann | A61F 2/442 623/17.12 |
| 2010/0331986 A1* | 12/2010 | Shikinami | A61F 2/30756 623/17.16 |
| 2011/0004307 A1* | 1/2011 | Ahn | A61F 2/441 623/17.12 |
| 2011/0029083 A1* | 2/2011 | Hynes | A61F 2/447 623/17.16 |
| 2011/0046740 A1* | 2/2011 | Chen | A61F 2/4455 623/17.16 |
| 2011/0245926 A1* | 10/2011 | Kitchen | A61F 2/4465 623/17.16 |
| 2011/0257748 A1* | 10/2011 | Liu | A61F 2/4425 623/17.16 |
| 2012/0065681 A1* | 3/2012 | DiLorenzo | A61B 17/7059 606/246 |
| 2012/0089230 A1 | 4/2012 | Buttner-Janz et al. | |
| 2012/0116513 A1* | 5/2012 | Carpenter | A61F 2/442 623/17.16 |
| 2012/0191189 A1* | 7/2012 | Huang | A61F 2/4425 623/17.11 |
| 2012/0215316 A1* | 8/2012 | Mohr | A61F 2/442 623/17.16 |
| 2012/0290089 A1* | 11/2012 | Melamed | A61F 2/442 623/17.16 |
| 2013/0013074 A1* | 1/2013 | Shikinami | A61F 2/442 623/17.16 |
| 2013/0023990 A1 | 1/2013 | Zipnick et al. | |
| 2013/0274884 A1* | 10/2013 | Matsumoto | A61F 2/44 623/17.16 |
| 2013/0274885 A1* | 10/2013 | Matsumoto | A61F 2/447 623/17.16 |
| 2013/0274886 A1* | 10/2013 | Matsumoto | A61F 2/442 623/17.16 |
| 2014/0277499 A1* | 9/2014 | Ainsworth | A61B 17/70 623/17.16 |
| 2014/0303736 A1 | 10/2014 | Roussouly et al. | |
| 2015/0045890 A1* | 2/2015 | Lefebvre | A61F 2/442 623/17.15 |
| 2015/0057755 A1* | 2/2015 | Suddaby | A61F 2/4425 623/17.16 |
| 2015/0257894 A1* | 9/2015 | Levy | A61F 2/442 623/17.15 |
| 2016/0000575 A1* | 1/2016 | Sawyer | A61F 2/442 623/17.16 |
| 2016/0022430 A1* | 1/2016 | Wickham | A61F 2/447 623/17.16 |
| 2016/0270931 A1* | 9/2016 | Trieu | A61F 2/30942 |
| 2016/0361177 A1* | 12/2016 | Biedermann | A61F 2/446 |
| 2017/0143502 A1* | 5/2017 | Yadin | B29C 64/153 |
| 2017/0143508 A1* | 5/2017 | Jensen | A61F 2/4425 |
| 2017/0258606 A1* | 9/2017 | Afzal | A61F 2/4465 |
| 2018/0078384 A1* | 3/2018 | Suddaby | A61F 2/4455 |
| 2018/0092754 A1* | 4/2018 | Jang | A61F 2/4455 |
| 2018/0228617 A1* | 8/2018 | Srour | A61F 2/442 |
| 2018/0235769 A1* | 8/2018 | Levy | A61F 2/4425 |
| 2018/0333272 A1* | 11/2018 | Mirda | A61F 2/4455 |
| 2018/0368981 A1* | 12/2018 | Mattes | A61L 27/045 |
| 2019/0000634 A1* | 1/2019 | Beale | A61F 2/44 |
| 2019/0038428 A1* | 2/2019 | Stauffer | A61F 2/4455 |
| 2019/0133783 A1* | 5/2019 | Unger | A61F 2/30771 |
| 2019/0274841 A1* | 9/2019 | Hawkes | A61F 2/442 |
| 2019/0314169 A1* | 10/2019 | Patel | A61F 2/30767 |
| 2019/0329544 A1* | 10/2019 | Yadin | B33Y 80/00 |

* cited by examiner

5700

DEVICE AND METHOD FOR CORRECTING SPINAL DEFORMITIES IN PATIENTS

CROSS-REFERENCE TO RELATED APPLICATIONS

The present application relies on the disclosures of and claims priority to and the benefit of the filing date of U.S. Provisional Application No. 62/715,638, filed Aug. 7, 2018. The disclosures of that application are hereby incorporated by reference herein in their entireties.

BACKGROUND

Field of the Invention

The present invention relates to methods and devices for correcting spinal deformities in humans and animals.

Spinal deformity, which typically includes transverse, lateral, and/or rotational misalignment of the vertebrae, can consist of various deformities, such as the following: kyphosis (exaggerated forward curvature of the upper spine), osteochondrosis (abnormal growth of the thoracic spine), scoliosis (abnormal curvature usually most notable in the coronal plane, but also including sagittal and rotational misalignment), and spondylolisthesis (displacement of lumbar vertebrae). Other factors resulting in spinal deformity may include, but are not limited to, fractures due to trauma and spondylitis. Techniques for correcting such deformities can be loosely divided into two categories, external and internal. External devices, such as braces, limit the mobility of the patient and are uncomfortable, resulting in low user compliance. Brace technology has therefore been inadequate to correct deformity and may prevent progression and in some cases induce worsened curvature.

Internal techniques for correcting deformity include the fusion of adjacent vertebrae through the immobilization of one or more vertebral element(s) and the distraction of the intervertebral disc space. In most cases, interbody cages and/or bone grafts are placed within the disc space to space the vertebrae and align them in an orientation that promotes fusion while also restoring the previous or desired angular relationship to achieve correct curvature of the spine. While many of these techniques are effective, fusion has negative effects on the range of motion of the patient and may, in cases, cause complications; sometimes severe complications. Furthermore, correction of deformities often requires fusion at multiple levels. Lastly, fusion on one level has so far been ineffective in correcting multilevel spinal deformity.

Thus, there exists a need for improved methods and devices for correcting spinal deformities while preserving motion capability and promoting user compliance.

Description of Related Art

U.S. Pat. Nos. 6,045,579 and 6,080,193 describe an "Adjustable Height Fusion Device," which comprises a method and apparatus for promoting spinal fusion between neighboring vertebrae. The apparatus is placed within the intervertebral space and preferably adapted to vary the distance between the engaging plates such that the height of the apparatus proximate the anterior end is greater than the height at the proximate the posterior ends, whereby the natural lordosis of the spine is maintained after the apparatus is installed. An alternative possibility describes the device containing struts with different heights in order to treat scoliosis. The current invention may have differing heights, but also contains an elastic section which applies forces for correction and is not intended for use in fusion.

The suite of U.S. patents, including U.S. Pat. Nos. 6,436,102, 6,447,548, 6,471,725, 6,562,047, 6,607,559, 6,740,119, 6,805,716, 6,837,904, 6,863,689, 6,890,356, 7,153,310, 7,217,292, 7,507,255, 7,550,008, 7,722,675, 8,038,717, 8,216,315, and 8,361,153, describe methods and implantation tools for a distraction method comprising distracting the space between vertebral bones by inserting a spacer, subsequently removing the spacer, and distracting with a wider spacer, all during one surgery. These spacers may be tapered, meaning the upper and lower surfaces are non-parallel such that the spacer comprises a wedge shaped implant. Such a wedge-shaped implant may be used to treat scoliosis by returning proper alignment to vertebral bones. Unlike such a technique covered by that suite of patents, the current invention is not intended for use in fusion and is not a rigid element.

U.S. Pat. No. 6,682,564 consists of an implant where the body may have a tapering height decreasing from the first end face to the second end face, and while also tapering more quickly in the first diagonal direction. The angle between the tapered top and bottom faces may vary depending on where the device is implanted within the spine. The current invention, while it may be wedged, is not a rigid body and is not intended for use in fusion.

U.S. Pat. No. 7,780,733 is an artificial spinal disc implant method for intervertebral disc replacement in which upper and lower brackets are joined together via springs connected to the upper bracket, which rest in spring guide tracks on the lower bracket. The device is intended to simulate the biological human disc. However, the current invention, in a preferred embodiment, uses springs to apply forces rather than absorb shock, which is unlike what is taught by the U.S. Pat. No. 7,780,733 patent and much of the prior art.

U.S. Pat. No. 7,922,767 describes an implant which promotes disc fusion via an inserted coil shaped device or devices. Such devices may be implanted simultaneously with varying heights providing a post-implantation configuration that optimizes the relative position between two vertebrae, thereby allowing for the treatment of scoliosis. The current invention, on the other hand, is not coil shaped and includes elastic sections between endplates.

U.S. Pat. No. 8,097,037 describes a method for correcting a spinal deformity comprising selecting two or more rigid body spinal implants from a plurality of spinal implants, each implant having a wedge-shaped configuration. The current invention taught herein may be wedge shaped, but is not a rigid body, and is intended for use in applying asymmetric forces to the vertebral column, unlike the U.S. Pat. No. 8,097,037 patented technology.

U.S. Pat. No. 8,118,873 describes an artificial vertebral joint for interposition between a superior vertebra and an inferior vertebra, wherein the superior posterior element is configured to engage and articulate with the inferior posterior element and a spacer extending between the superior component and the inferior component, where the spacer may contain an internal mesh component with an elastic core. The current invention may have an elastic core, but, in embodiments, comprises multiple sections for applying asymmetric forces in addition to acting as a shock absorber.

U.S. Pat. No. 8,366,776 comprises a tapered vertebral implant for use in establishing desired spinal curvatures including separate implant bodies. The bodies may include an associated angle between inferior and superior surfaces of the body and may be stacked so that the associated angles are oriented in a different anatomical plane. Such orientation could provide a rigid fixture for fusion in a preferred alignment. The current invention is not rigid as it contains an elastic section and is not intended for fusion.

U.S. Pat. No. 8,377,138 is an intervertebral disc replacement device in which an artificial intervertebral disc is placed within the interbody space. The disc is made up of two parts, where the inner portion is the nuclear area and the outer portion is for structural support. The device may also include a coiled compression spring in the internal disc to provide support; additionally, endplates can be positioned in a wedge shape. The current invention contains an outer portion which is designed not to mimic the annulus of the disc and act in compression, but to actually apply forces to the adjacent vertebrae through extension of a compressed material to realign the vertebrae rather than merely provide the natural space and support between them.

U.S. Pat. No. 8,382,838 is an interbody vertebral replacement in which an elastic center part surrounded by a fibre system is fit into the space between adjacent vertebrae. The center part can be compressed axially by loading in the vertebral column causing a bulge that is restricted by the fibre system, thereby mimicking the in vivo intervertebral disc. Unlike the current invention, the interbody vertebral replacement is only designed to absorb shock. The current invention not only may absorb shock, but it also may contain multiple discrete springs or polymer springs to apply forces to the adjacent vertebrae through extension of a compressed material to realign the vertebrae in addition to responding to the natural loading and movement of the spine.

U.S. Pat. No. 9,034,045 describes an expandable interbody implant device for separating two vertebrae and promoting fusion. The implant complains ramps so that lordosis may be matched. One side of the ramp can be shorter than another side of the ramp with a corresponding difference along ramps. In this manner, a sideways orientation of the spine may be corrected. This device results in fusion of the vertebrae; it is also important to note most deformity is not merely a deformation in the coronal plane. The current invention is not intended for fusion and additionally corrects deformity in more than one plane.

In the above-mentioned patents, it is either claimed or hypothesized that scoliosis may be treated by expansion or applying forces in one plane. However, scoliosis is not a single planar disease. Furthermore, implantation of a rigid, wedge shaped device or a device that may be configured into a wedged shape will result in the fusion of the adjacent vertebrae, which will A) likely not result the correction of scoliosis due to an inability of the static forces to overcome the forces causing or linked to scoliosis, and B) result in the known presence of adjacent level disease, in which fusion at one level results in degeneration and disequilibrial forces at the adjacent levels. It is noteworthy that a dynamic system, such as that taught herein, will facilitate the correction of scoliosis without fusing the vertebrae.

SUMMARY OF THE INVENTION

The present invention is directed to specific devices and methods intended for use in the correction of spinal deformity. In one exemplary embodiment, a method for correcting spinal deformity comprises inserting a spinal implant into the disc space formed by adjacent vertebrae. The disc space may have a lateral side adjacent to the concave side of curvature along the vertical axis of the spine (the concave-lateral side) and a lateral side adjacent to the convex side of a curvature along the vertical axis of the spine (the convex-lateral side). The concave-lateral side may be of a lower height than the convex-lateral side due to the curvature of the spine. The method of treating spinal deformity presented in this invention describes the use of asymmetric forces applied to the adjacent vertebrae to realign the vertebral segment and have those forces thereby propagate through the spinal column. The method uses the restoring force of the spring as defined by Hooke's law. If an elastic material is compressed or expanded, thereby becoming displaced, it will exert a force such that it can be restored to its initial position.

The spinal implant used to induce such forces may be comprised of a top and bottom face with a polymer spanning from the top face to the bottom face to be intraoperatively wedged and then inserted in said disc space so that the height of the implant is higher on the concave-lateral side and lower on the convex-lateral side. The polymer may be elastic so that the implant desires to expand on the concave-lateral side and compress on the convex-lateral side, drawing the vertebrae into alignment. The spinal implant can have a footprint that matches or resembles the footprint of the endplates of the adjacent vertebrae, with ridges that increase the surface area between implant and vertebrae to allow for frictional fixation. Forces exerted by the implant may propagate through the spinal column to align vertebrae adjacent to those directly adjacent to the implant.

In another embodiment, an implant is provided that may have a polymer region where the polymer itself is preoperatively wedged so that it is higher on the concave-lateral side and lower on the convex-lateral side.

In a further embodiment, an implant is provided that may have a region interior to the polymer—between the two faces and in some configurations with the polymer—that has an elastic property that matches or resembles the elastic, shock absorbing properties of the previous disc. The interior region may be positioned in a cylindrical area more central than the polymer.

In yet another embodiment, a polymer, as provided, may be divided in multiple sections, so that each section may have a differing height, or each section may have a different elastic property so as to more accurately apply forces that may draw the vertebra into their proper alignment.

In another embodiment, the implant described herein may have discrete springs organized around the interior elastic region, made of metal or polymer, instead of solid polymer springs.

In another embodiment, the device may have spikes, bumps, or similar protrusions that allow for surface matching that creates a frictional interface that promotes fixation of the top and bottom faces to the endplates of the adjacent vertebrae.

The present invention may also be attached to the endplates of adjacent vertebrae via a screw or other fixation system, in certain aspects, where one or more screws may be inserted through threads in either the top or bottom face or both faces and into the endplate. The screws may also be inserted through a protrusion of the implant that exists parallel to a vertical face of an adjacent vertebrae.

The implant described may also exist in multiple sections that are inserted via routes on opposite or varying sides of the spine, having footprints matching or resembling the lateral half of the adjacent vertebral endplate. The implants may or may not connect to the one another via one or more mechanisms, including but not limited to a dowel-to-hole connection, hooks, magnets, and/or screws.

The present invention also describes an implant which consists of a first element which may be comprised of a top and bottom face with a polymer spanning from the top face to the bottom face. The element may be connected via a hinge to a second element which may be comprised of a top and bottom face with a polymer spanning from the top face to the bottom face. The implant may be inserted so that the central axis of the first element is aligned with that of the second element and then the first element is rotated via a mechanism around the hinge so that it may exist parallel to the second within the disc space.

In another embodiment, an implant is provided that may exist in a smaller version, so that two or more similar implants may be inserted via opposite or varying sides of the spine and connected.

BRIEF DESCRIPTION OF THE DRAWINGS

The accompanying drawings illustrate certain aspects of embodiments of the present invention and should not be used to limit the invention. Together with the written description the drawings serve to explain certain principles of the invention.

DETAILED DESCRIPTION OF VARIOUS EMBODIMENTS OF THE INVENTION

Various embodiments will now be described in detail to provide an understanding of the structure, function, manufacture, and use of the devices and methods disclosed herein. It should be understood that the following discussion of exemplary embodiments is not intended as a limitation on the invention; rather, the following discussion is provided to give the reader a more detailed understanding of certain aspects and features of the invention.

One or more examples of the embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. It will be to those that various modifications and variations can be made in the practice of the present invention without departing from the scope or spirit of the invention; the features illustrated or described in connection with one exemplary embodiment may be combined with the features of other embodiments. Such modifications and variations are intended to be included within the scope of the present invention. All references cited in this application are hereby incorporated by reference in their entireties.

The current invention describes methods and devices for correcting spinal deformities, and in particular, correcting abnormal curvature including most cases of spinal deformity. In embodiments, one or more dynamic implants which exist in a wedge-shaped configuration or exert asymmetrical force to correct wedging are provided. In an exemplary embodiment, one or more implants can be positioned between adjacent vertebra at the apex of curvature to increase the height of the disc space on the concave side and decrease that on the convex side by dynamically applying continuous forces to the endplates of the adjacent vertebrae over time.

Figure 1A:
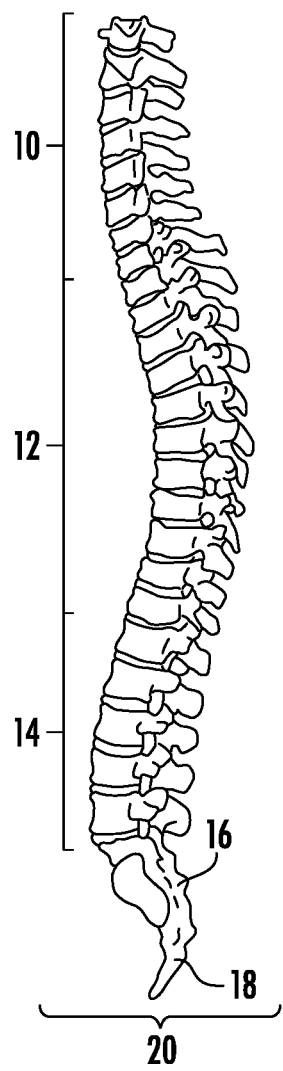
FIG. 1A depicts the spinal column in the coronal plane from the posterior view.
Figure 1B:
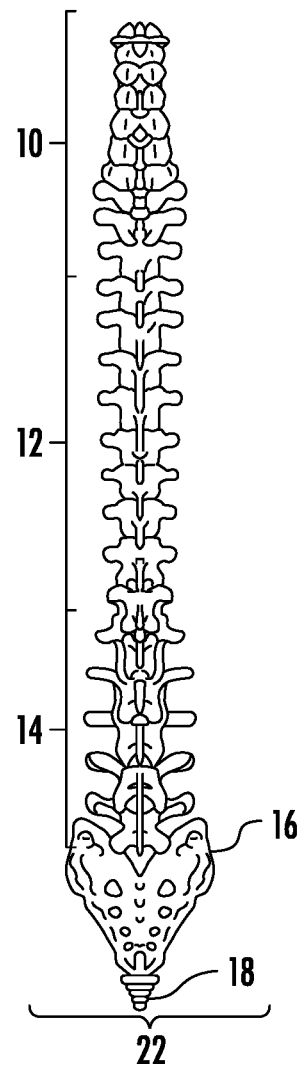
FIG. 1B depicts the lateral view of the spinal column in the sagittal plane.
Figure 1C:
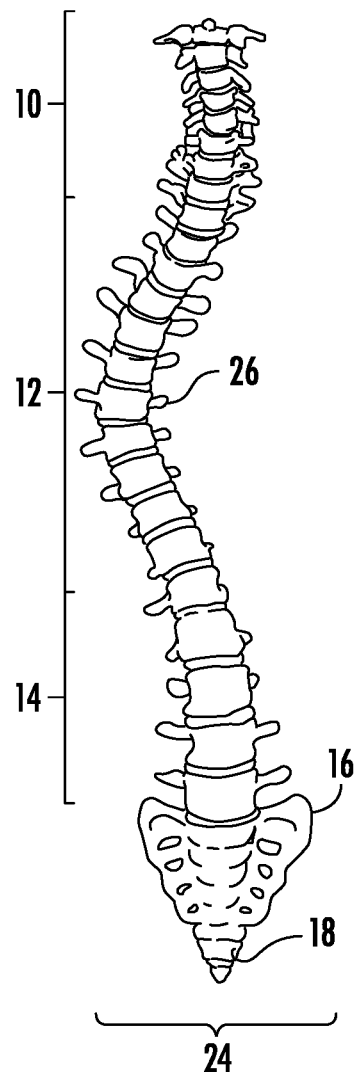
FIG. 1C depicts an example case of spinal deformity in the coronal plane.
Figure 1D:
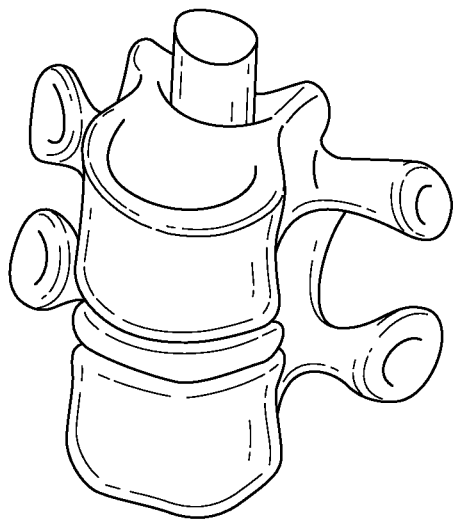
FIG. 1D depicts a vertebral segment from an isotropic view.
Figure 1E:
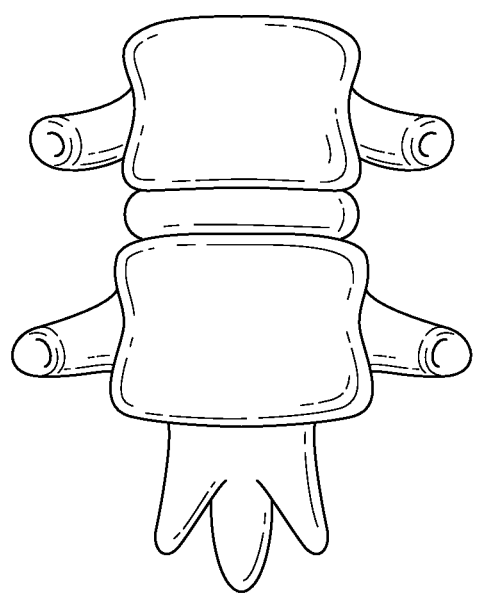
FIG. 1E depicts a vertebral segment from an anterior view.
Figure 1F:
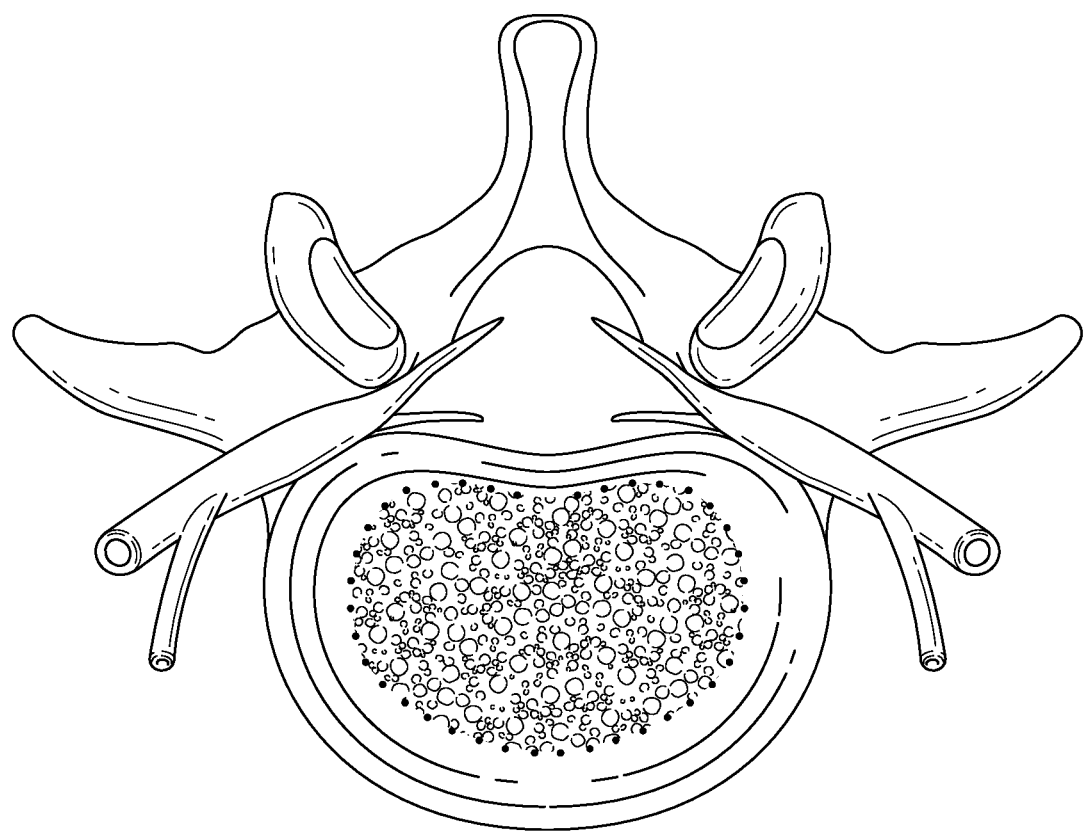
FIG. 1F depicts a cross section of a typical vertebra.

Normal spinal orientation is depicted in FIG. 1A-B. In FIG. 1A, the spine is viewed posteriorly as it exists in the coronal plane (20) and in FIG. 1B, the spine is viewed laterally as it exists in the sagittal plane (22). The spine consists of 7 cervical vertebrae (10), 12 thoracic vertebrae (12), 5 lumbar vertebrae (14), the sacrum (16), and the coccyx (18). Spinal deformity typically occurs in some region between the thoracic and lumbar vertebrae. An example of spinal deformity, scoliosis, is shown in FIG. 1C in a posterior view as would be seen in the coronal plane (24) with the apex of curvature located in the thoracic region (26). In FIG. 1D-E, a single vertebral segment is shown; the vertebral segment comprises a top and bottom vertebra as well as the disc in between and the muscles and ligaments attached to the top and bottom vertebrae. In an embodiment, the current invention acts directly on the vertebrae of a single vertebral segment, through which forces may propagate to act on adjacent vertebral segments. A cross sectional view of this vertebral segment is shown in FIG. 1F.

Figure 2A:
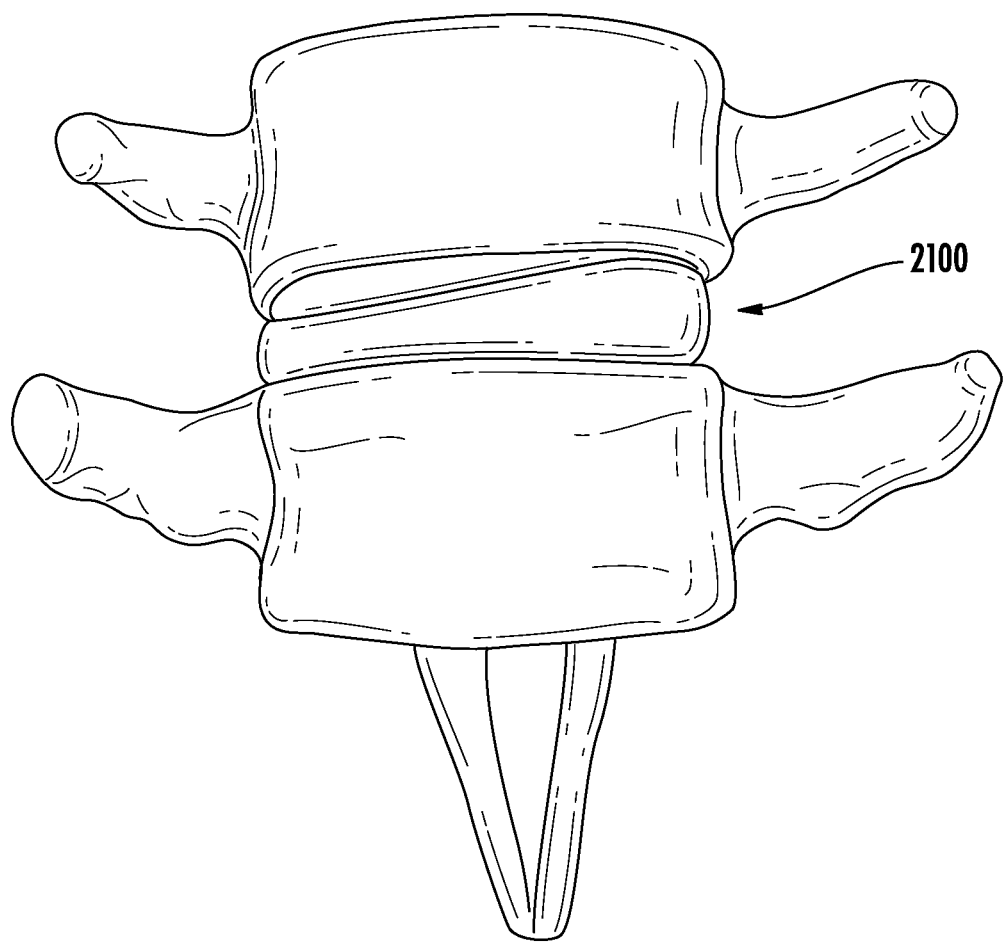
FIG. 2A depicts an exemplary method for treatment of deformity using asymmetrical forces from a coronal view.
Figure 2B:
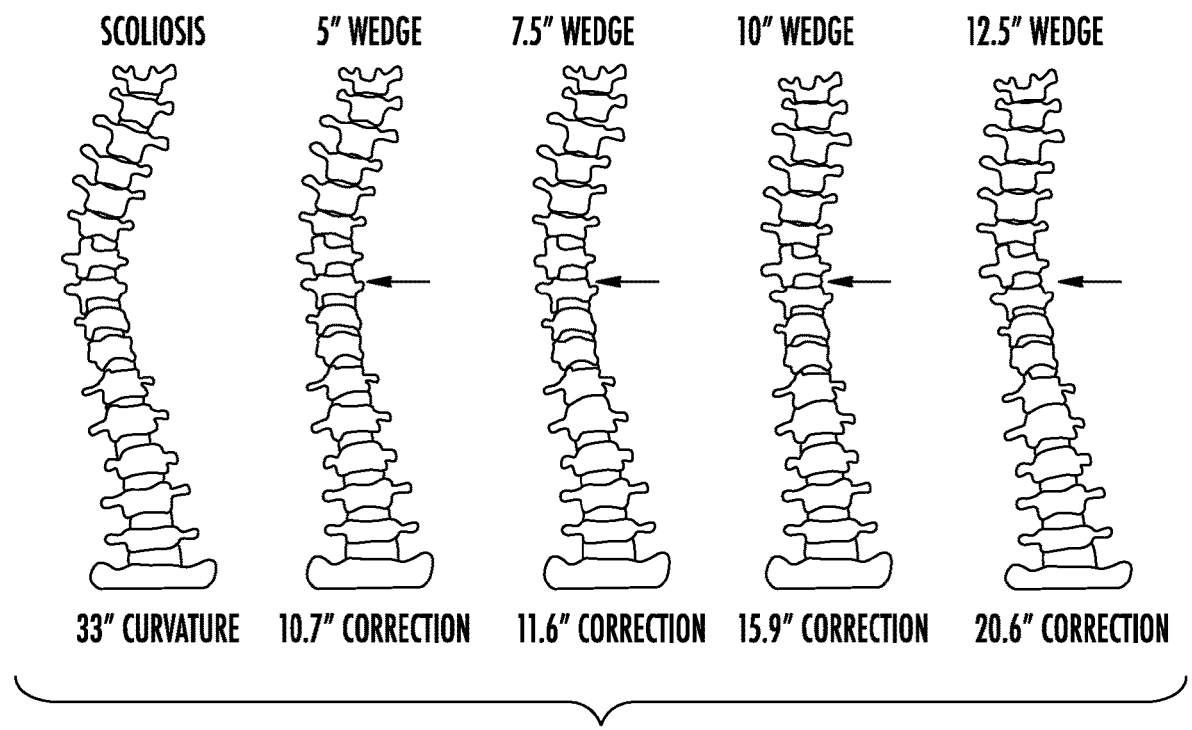
FIG. 2B depicts the correction achieved using various wedged angle constructs expanding upon this embodiment.
Figure 2C:
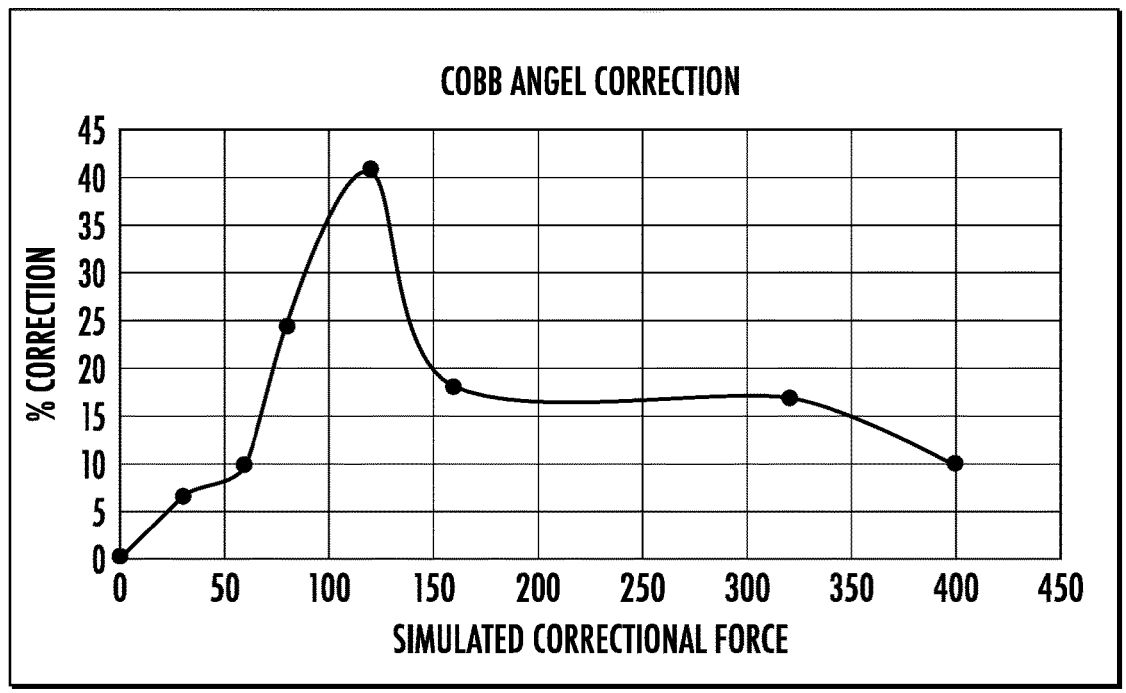
FIG. 2C depicts optimization of the corrective force.

In one embodiment, the current invention comprises a method by which an expansive force is applied to one or more concave aspects of the vertebral segment. A tensile force may also be applied to one or more convex aspects of the vertebral segment. Such forces increase disc space height in concave aspects of the vertebral segment and decrease disc height in convex aspects of the vertebral segment. As shown in FIG. 2A, the forces may result in the realignment of the vertebral segment, which may lead to a propagation of forces through the spinal column, realigning other aspects of the column. In this method, a part of the disc or the whole disc would be removed so as to insert an implant (2100) which could apply such forces. FIG. 2B depicts correction achieved using various wedged angle constructs expanding upon this embodiment. FIG. 2C presents data from a pilot study of force optimization in applying a corrective force to the spinal column from within the disc space. Optimal correction curve was found to be within the range of 80 to 160N, with maximum correction occurring at 120N. Force above this range caused over correction, and those below caused undercorrection. Thus, the current method would involve the application of forces as described above and herein within a similarly optimized range.

Figure 3A:
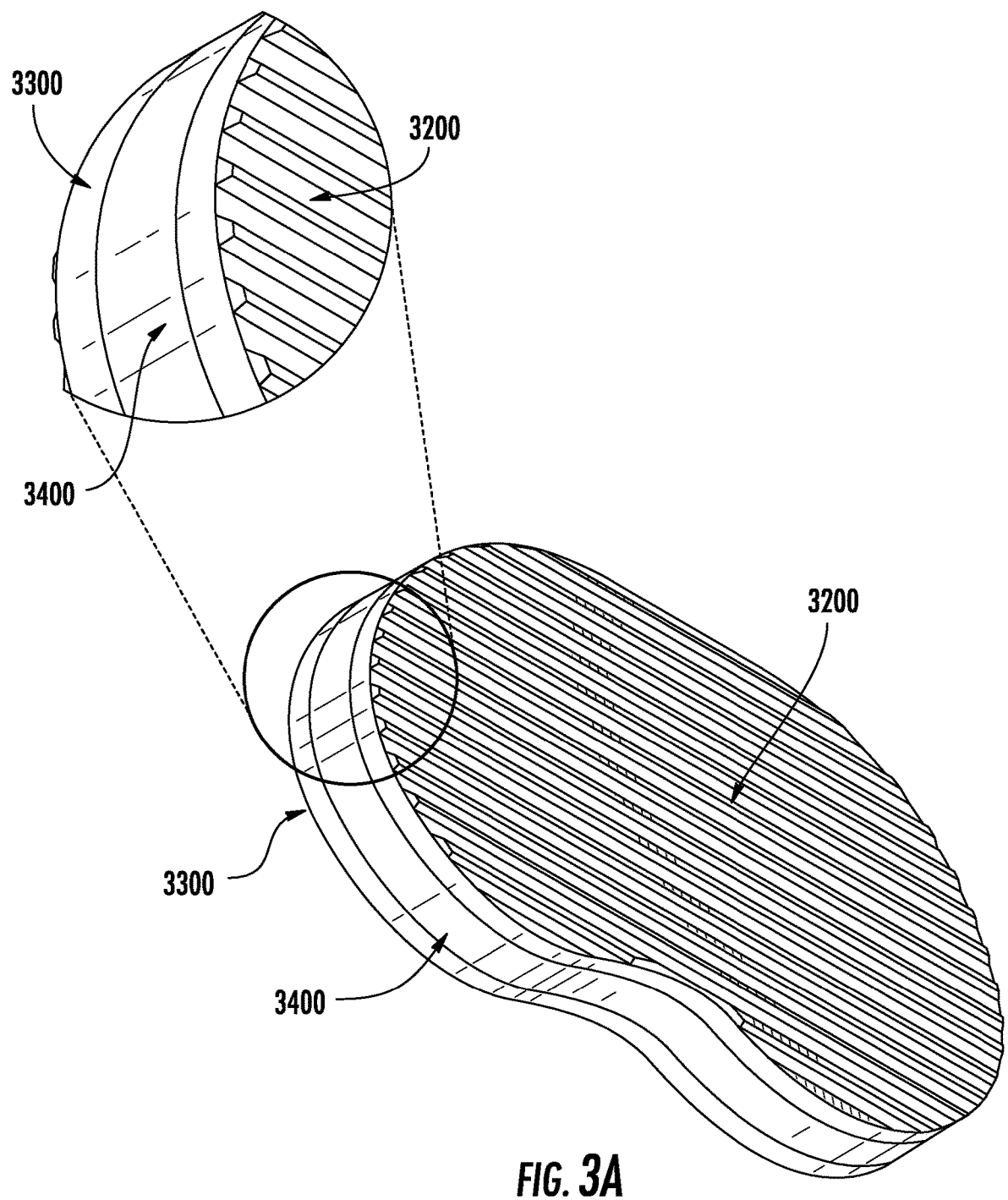
FIG. 3A depicts an exemplary embodiment of the device from an isotropic view.
Figure 3B:
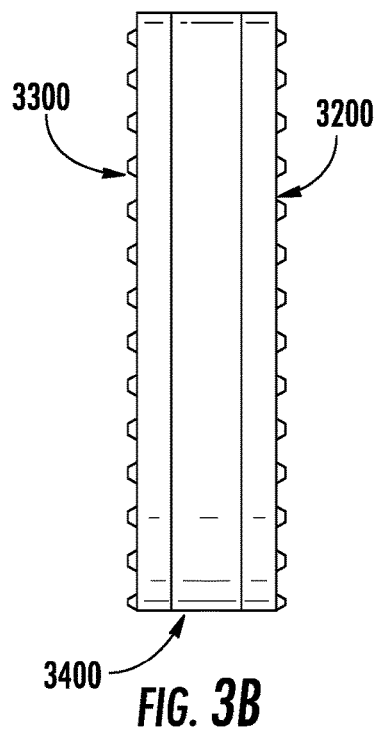
FIG. 3B depicts an exemplary embodiment from a side view.
Figure 3C:
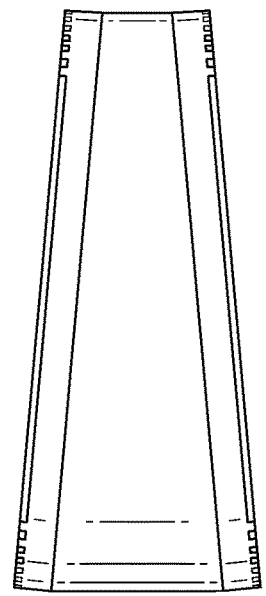
FIG. 3C depicts an exemplary embodiment from a side view where the polymer is preoperatively wedged.
Figure 3D:
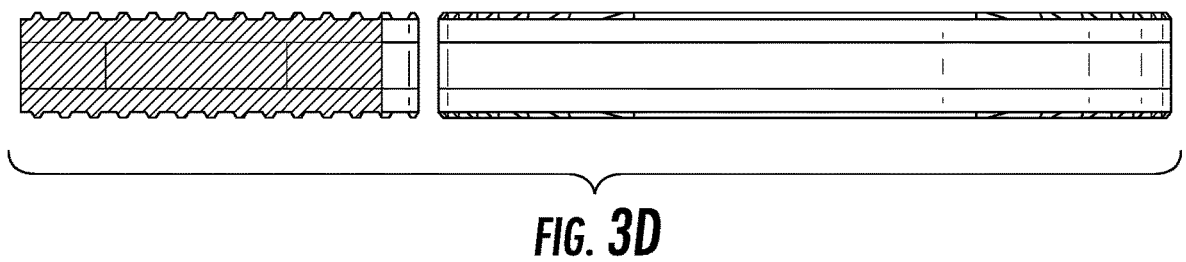
FIG. 3D depicts a cross sectional view of an exemplary embodiment.
Figure 3E:
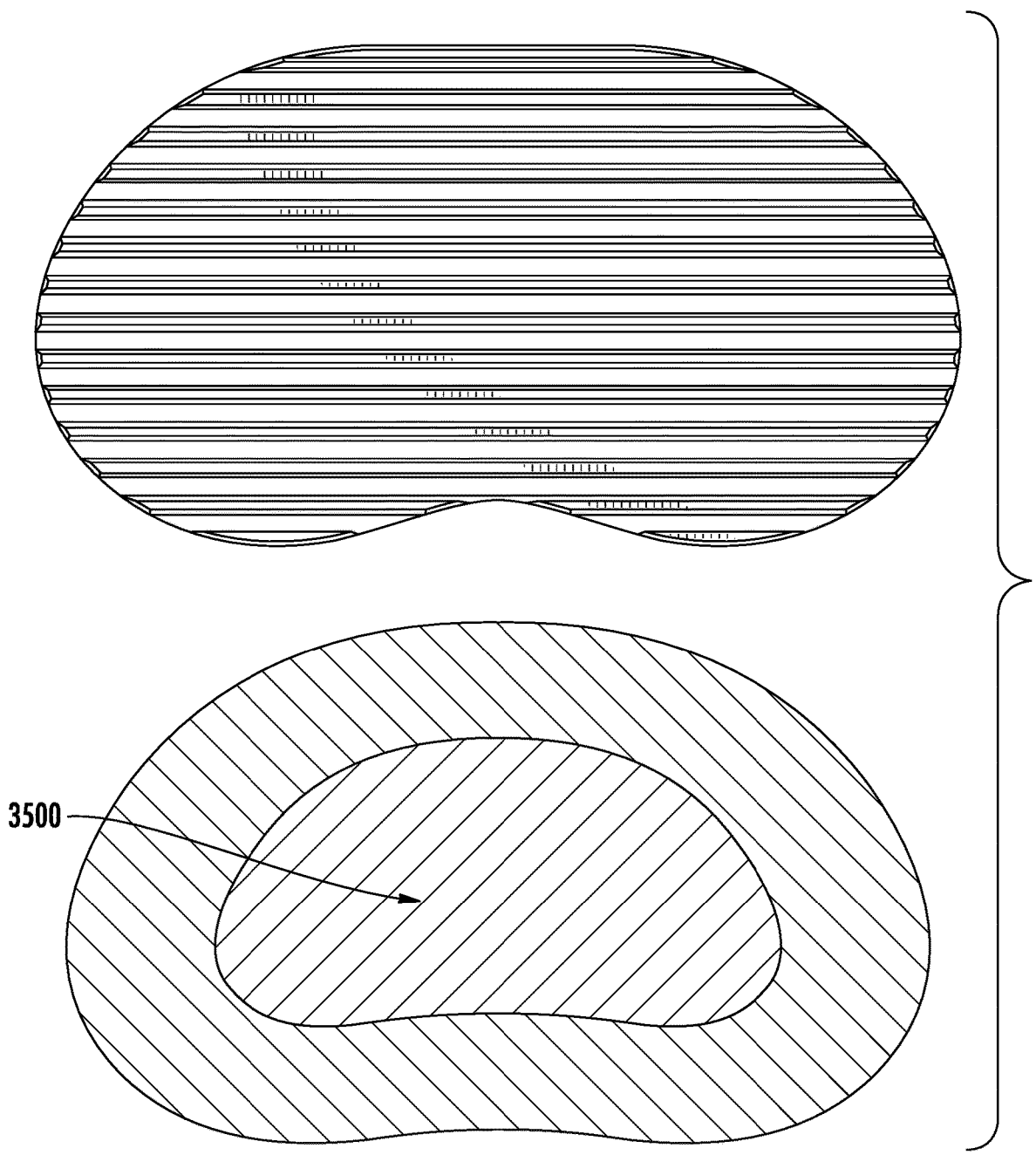
FIG. 3E depicts a cross sectional view from a vertical viewing plane of an exemplary embodiment in which there exists an internal elastic region, and a cross sectional view of an exemplary embodiment from a horizontal viewing plane.
Figure 3F:
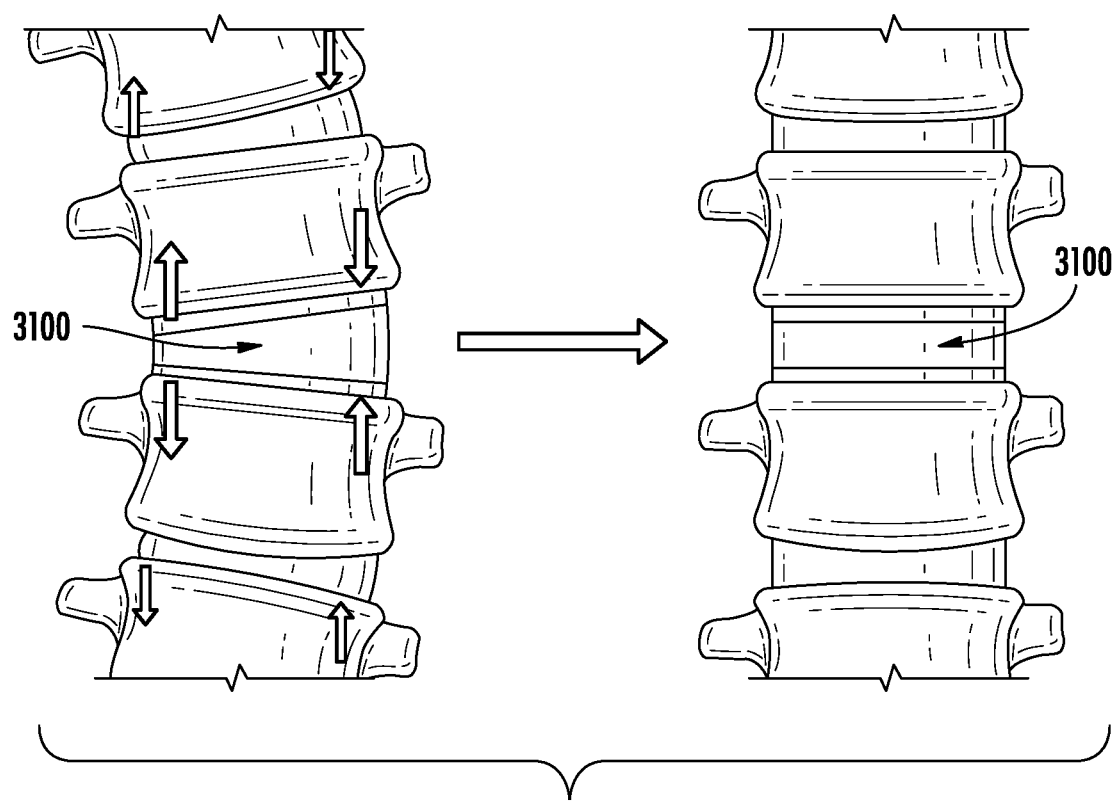
FIG. 3F depicts an example of an insertion of said embodiment into the vertebral column.

In aspects, the implant, which may engage in such a method of correction of deformity, may have various properties. One exemplary embodiment is shown in FIG. 3A-D, in which the device has a top plate (3200) and bottom plate (3300) with an elastic section in the middle (3400); this section may be an elastic polymer. Such internal section, in a preferred aspect, is what applies the forces to the adjacent vertebra above and below the device. As shown in FIG. 3D, the cross-sectional area, in aspects, is of the same, similar, or approximate footprint, shape, or form as that of the vertebrae, so that it completely or partially matches the vertebral segment. The elastic section may have an internal region (3500) which is less stiff and matches the elastic properties of the disc (e.g., FIG. 3E) to act as a shock absorber. The insertion of such device (3100) into the disc space is shown in FIG. 3F; the device, in aspects, uses resultant forces to the wedging of the vertebrae that pushed the concave aspects apart. According to data from a pilot study of force optimization for such an elastic region in correcting a scoliotic curve, a factor of 200 was added to the force to account for the normal axial loading of the spine. This value was derived based on research carried out by Izamburt et al., in which IVDs were preloaded with 400 N of force to mimic axial loading of an adult spine. This value was halved to account for the lighter weight of the targeted pediatric patient population. Required Young's modulus was determined to be 8.67 MPa. The elastic modulus in a preferred embodiment of the current invention resembles that of the natural intervertebral disc, which lies within 5.8-42.7 MPa. This, however, may be a result of the small Cobb angle generated by current simulations. The required elastic modulus for this material may be calculated in a similar manner to determine material characteristics of such an embodiment, and/or other embodiments presented herein.

Figure 4A:
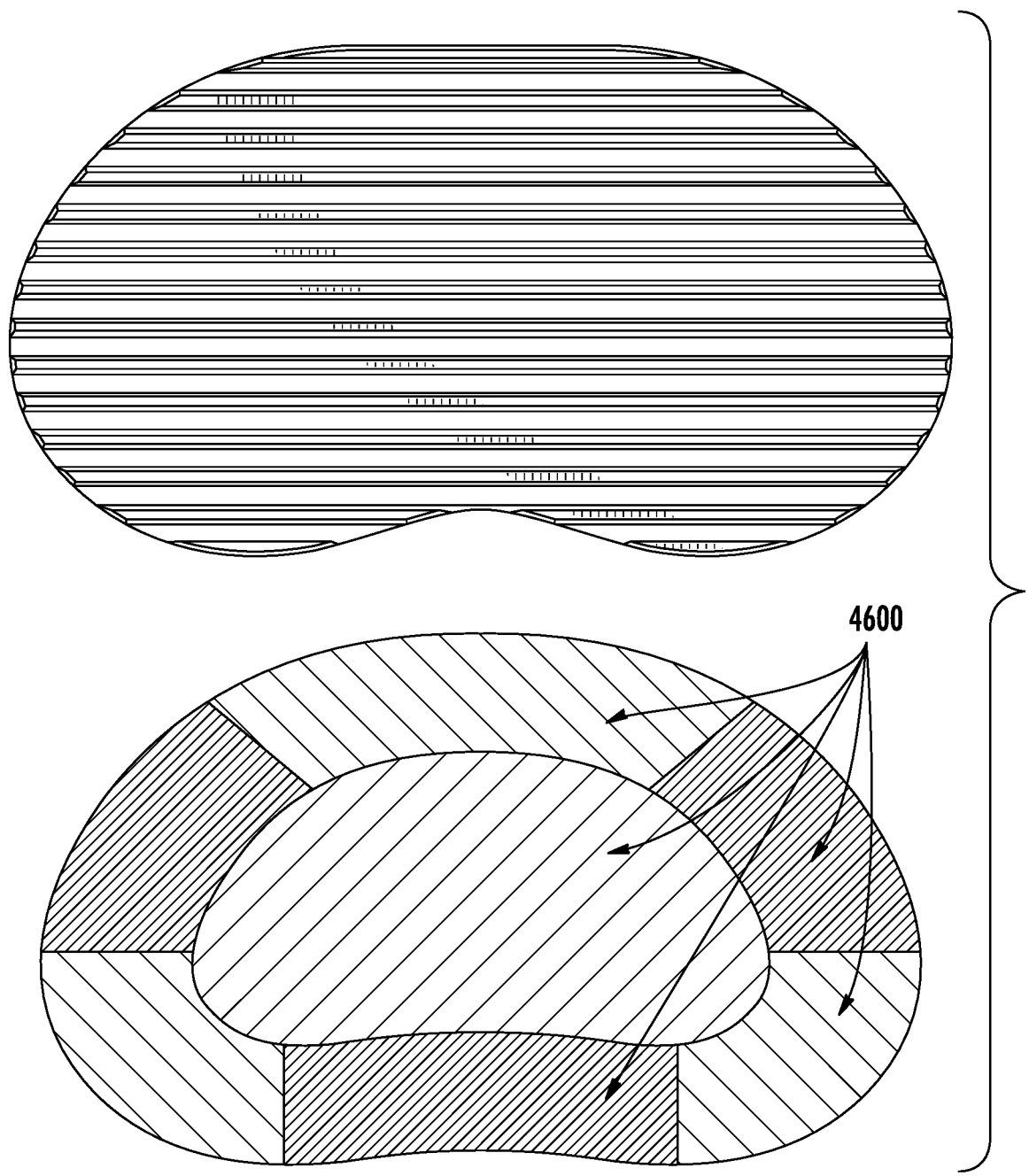
FIG. 4A depicts a cross sectional view of an exemplary embodiment where there exist multiple polymer sections.
Figure 5A:
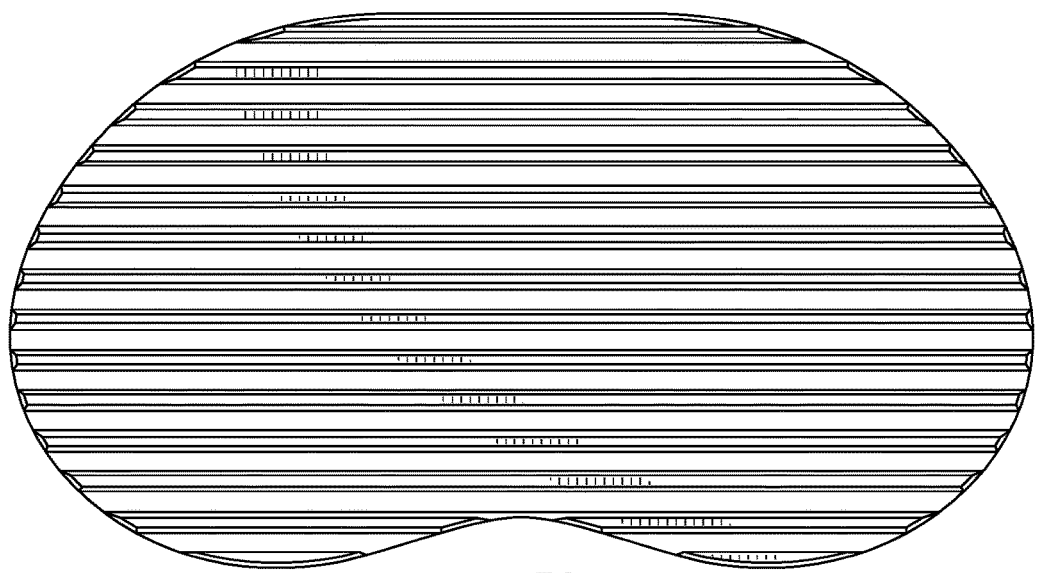
FIG. 5A depicts a cross sectional view of an exemplary embodiment where there exist multiple discrete spring sections.
Figure 5B:
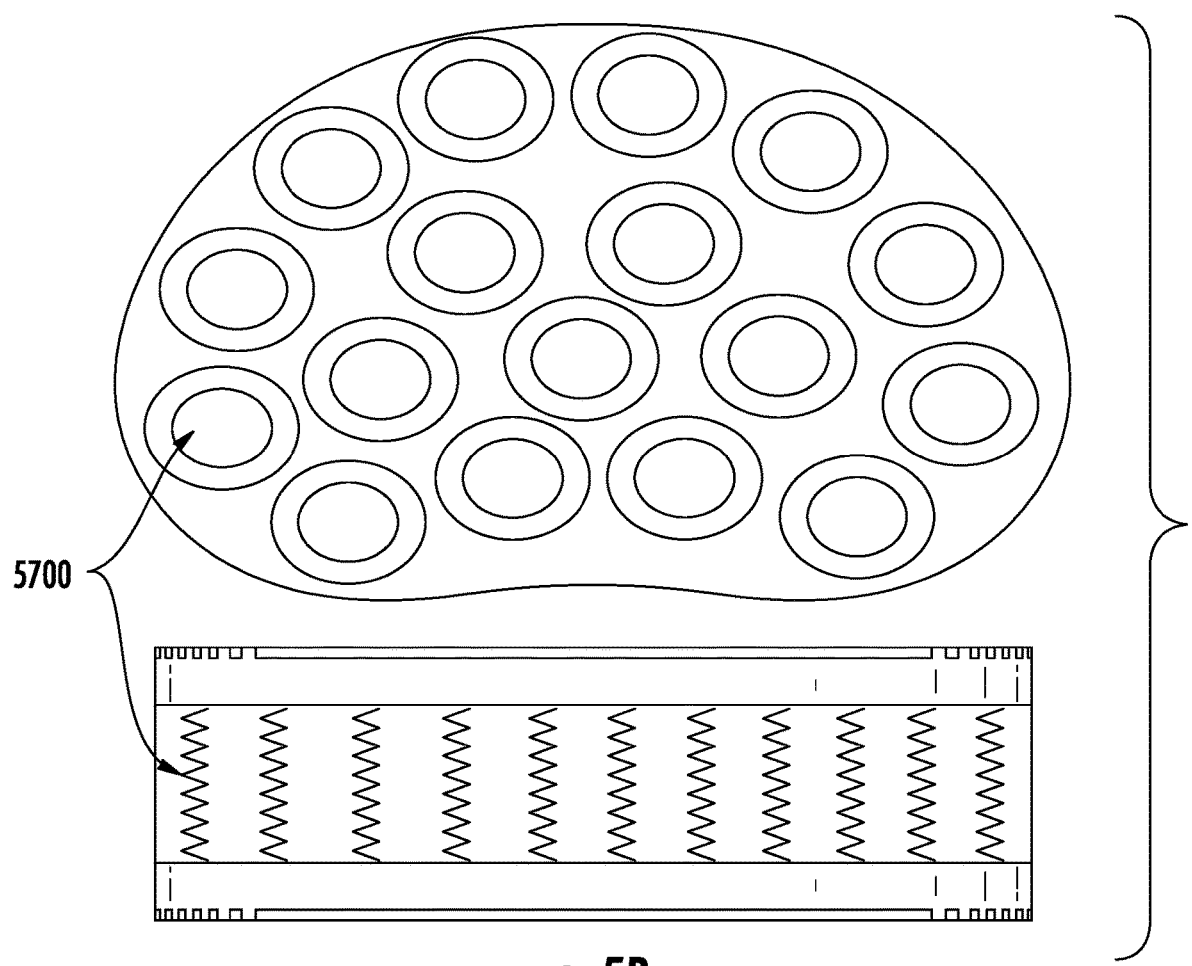
FIG. 5B depicts a side view of an exemplary embodiment where there exist multiple metal spring sections.

In one embodiment, the device may comprise multiple polymer sections (4600) in various shapes depending on what force(s) are desired to be applied and where on the endplates of the adjacent vertebrae the force(s) must or should be applied (see, e.g., FIG. 4A). Such a device may have shorter elements that pull one or more aspects of the vertebrae together through a tensile force or longer elements that push aspects of the vertebrae apart, by way of example. Instead of polymer springs, the device may include discrete springs (5700) (see, e.g., FIG. 5A-B).

Figure 6A:
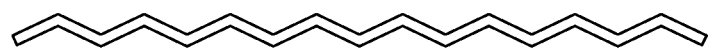
FIG. 6A-C depicts differing frictional surfaces taught herein.
Figure 6B:
Figure 6C:

In order for the device to remain within the disc space, it is preferable, in embodiments, to have as much of a contact with the adjacent vertebrae as possible to create a frictional interface between the plates of the device and the endplates of the adjacent vertebrae. A variety of interfaces can increase the surface area including ridges (see, e.g., FIG. 6A), spikes (see, e.g., FIG. 6B), bumps (see, e.g., FIG. 6C), or other similar protrusions.

Figure 7A:
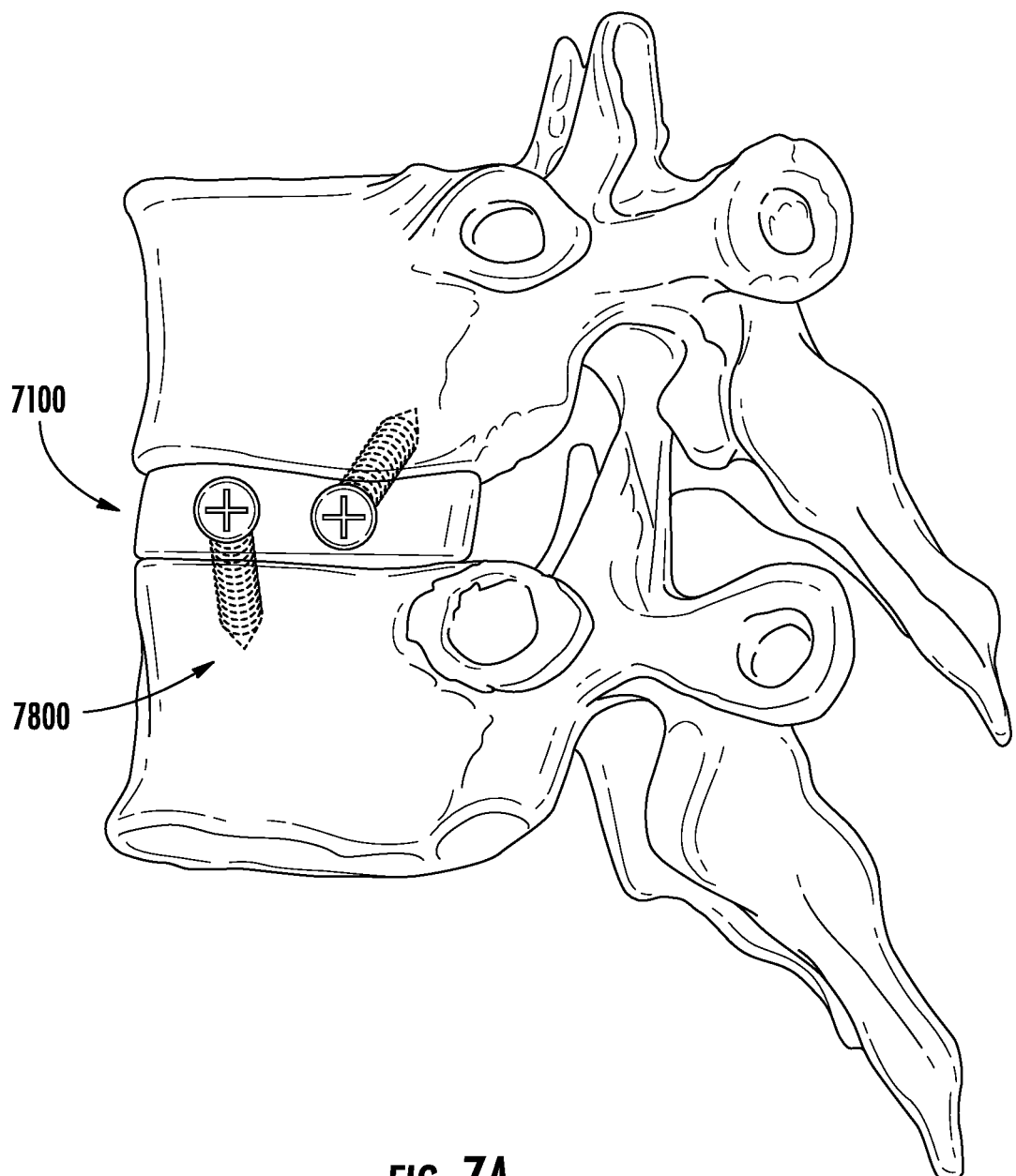
FIG. 7A depicts a combination with screw implantation from a side view.
Figure 7B:
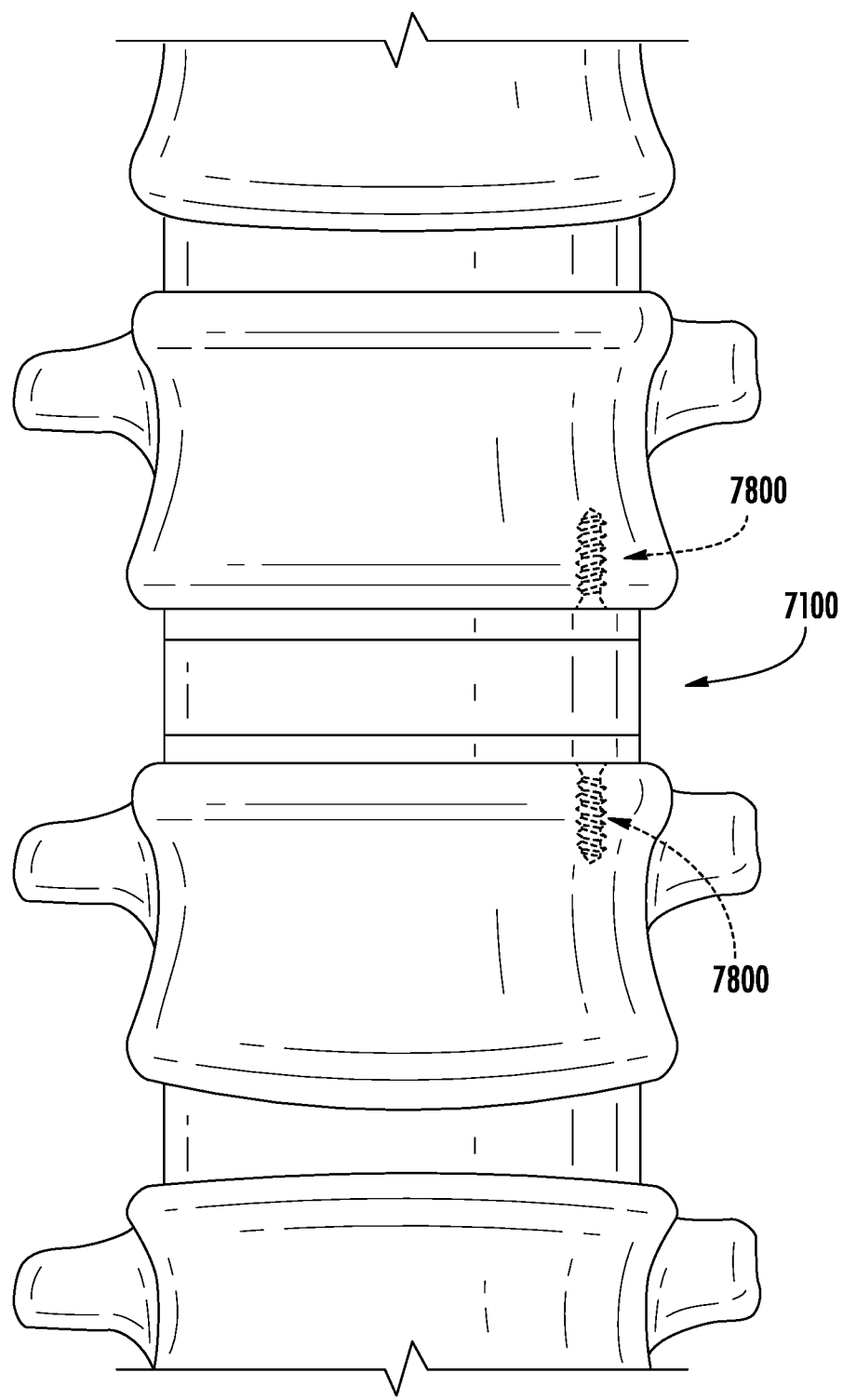
FIG. 7B depicts a combination with screw implantation from an anterior view.

In order to apply a compressive force, it may be necessary to attach the implant (7100) to the adjacent vertebrae via a screw, attachment, or similar, system (7800) (see, e.g., FIG. 7A-B). In embodiments, one or more screws or other attachment mechanisms may be inserted through a protrusion of one or both or more plates of the implant or through the one or both or more of the plates of the device itself.

Figure 8A:
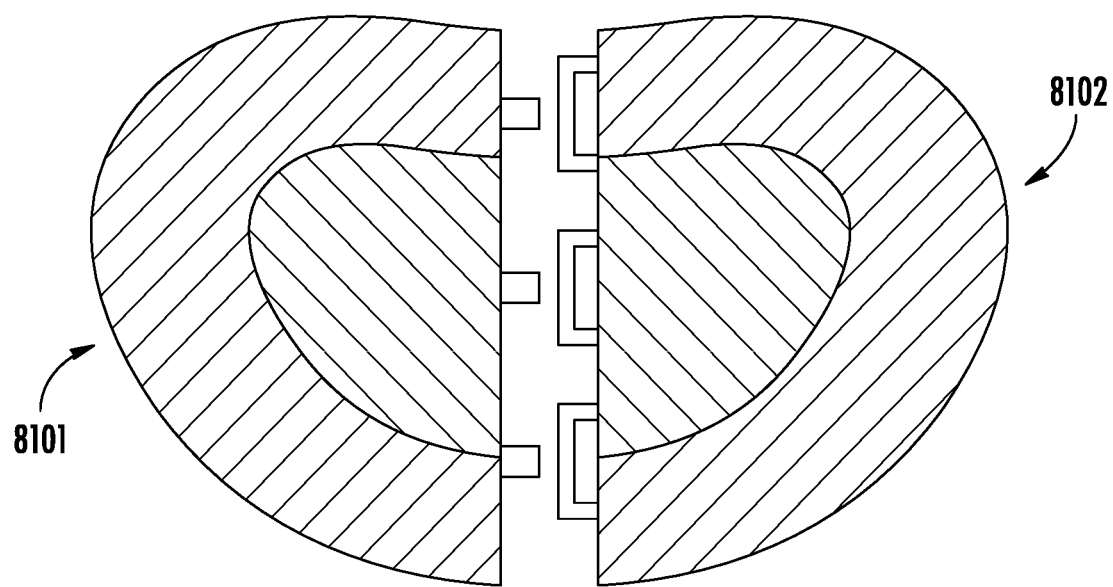
FIG. 8A depicts an embodiment where multiple device sections are inserted and may join from a top view.
Figure 8B:
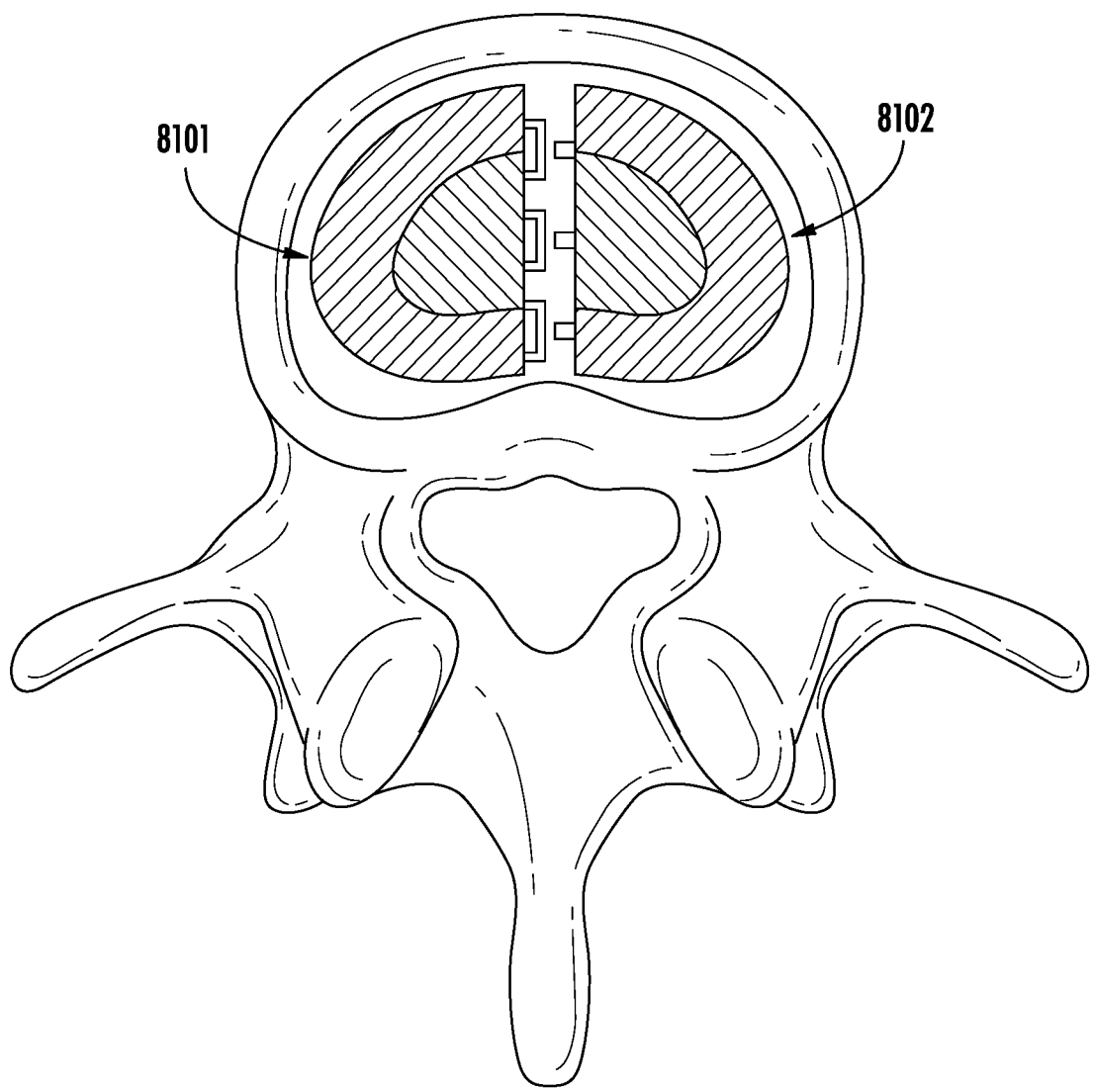
FIG. 8B depicts a possible insertion of the multiple device sections.
Figure 8C:
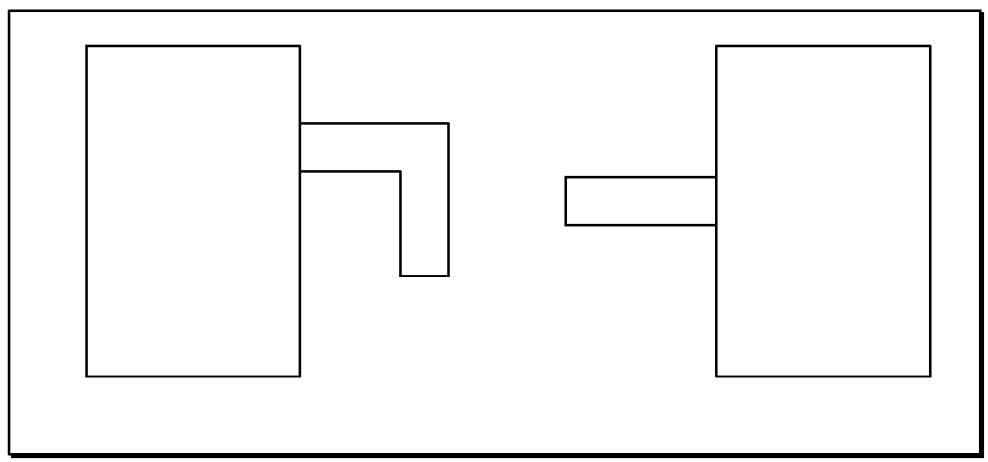
FIG. 8C depict a possible connection mechanism of the multiple device sections.

The device may comprise a configuration in which it is divided into two or more parts that make separate implants (8101 and 8102), or two or more parts of the same implant which can be inserted from two or more sides of the disc space (see, e.g., FIG. 8A-B). The device may exist as two or more separate implants (or parts of the same implant) within the space, or may be connected via one or more connecting mechanisms including, but not limited to, hooks or screws, by way of example only. (See, e.g., FIG. 8C).

Figure 9A:
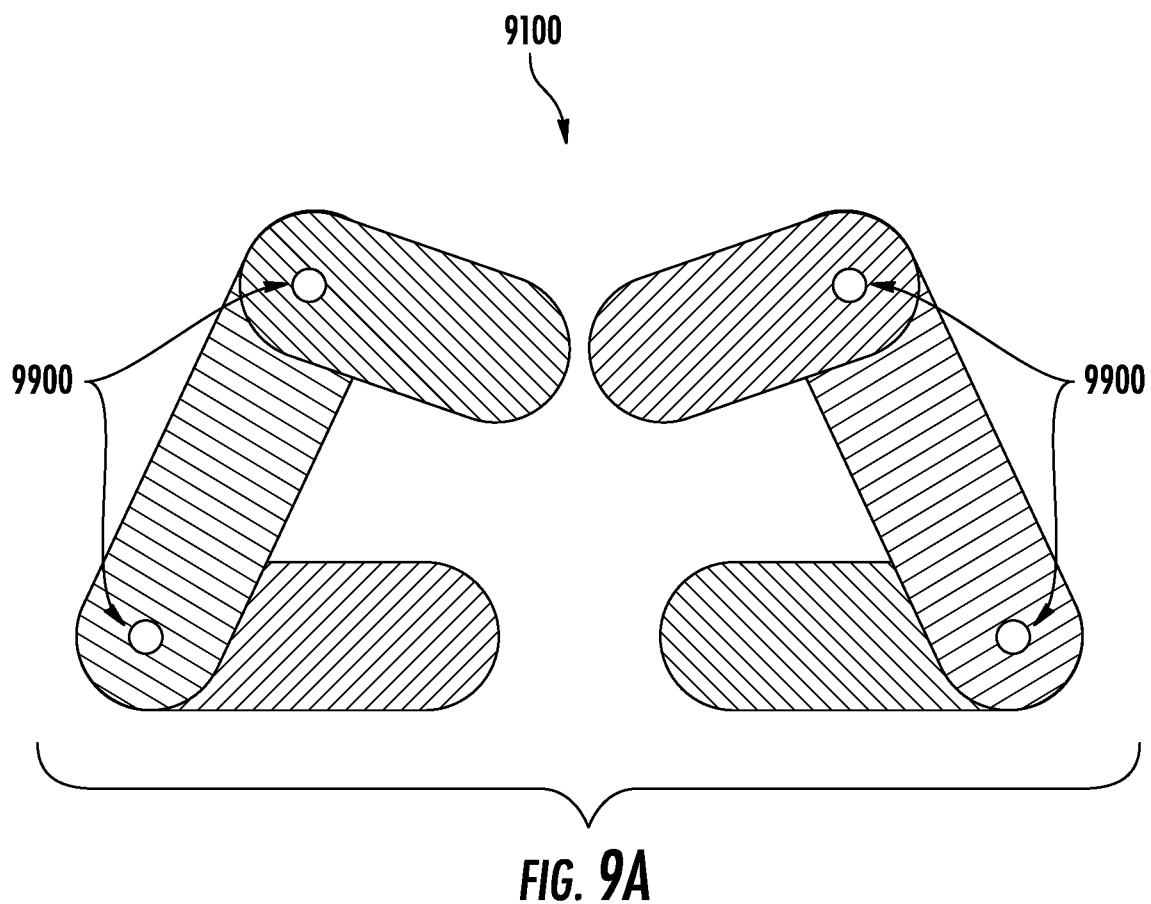
FIG. 9A depicts the hinge-mechanism embodiment from a top view.
Figure 9B:
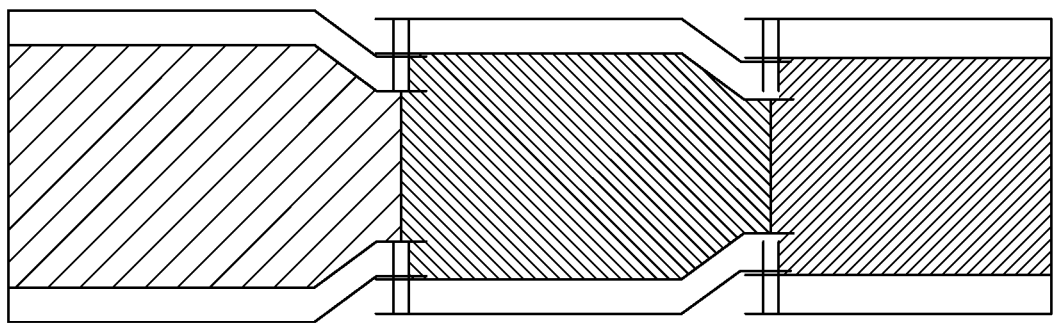
FIG. 9B depicts the hinge-mechanism embodiment from a side view.
Figure 9C:
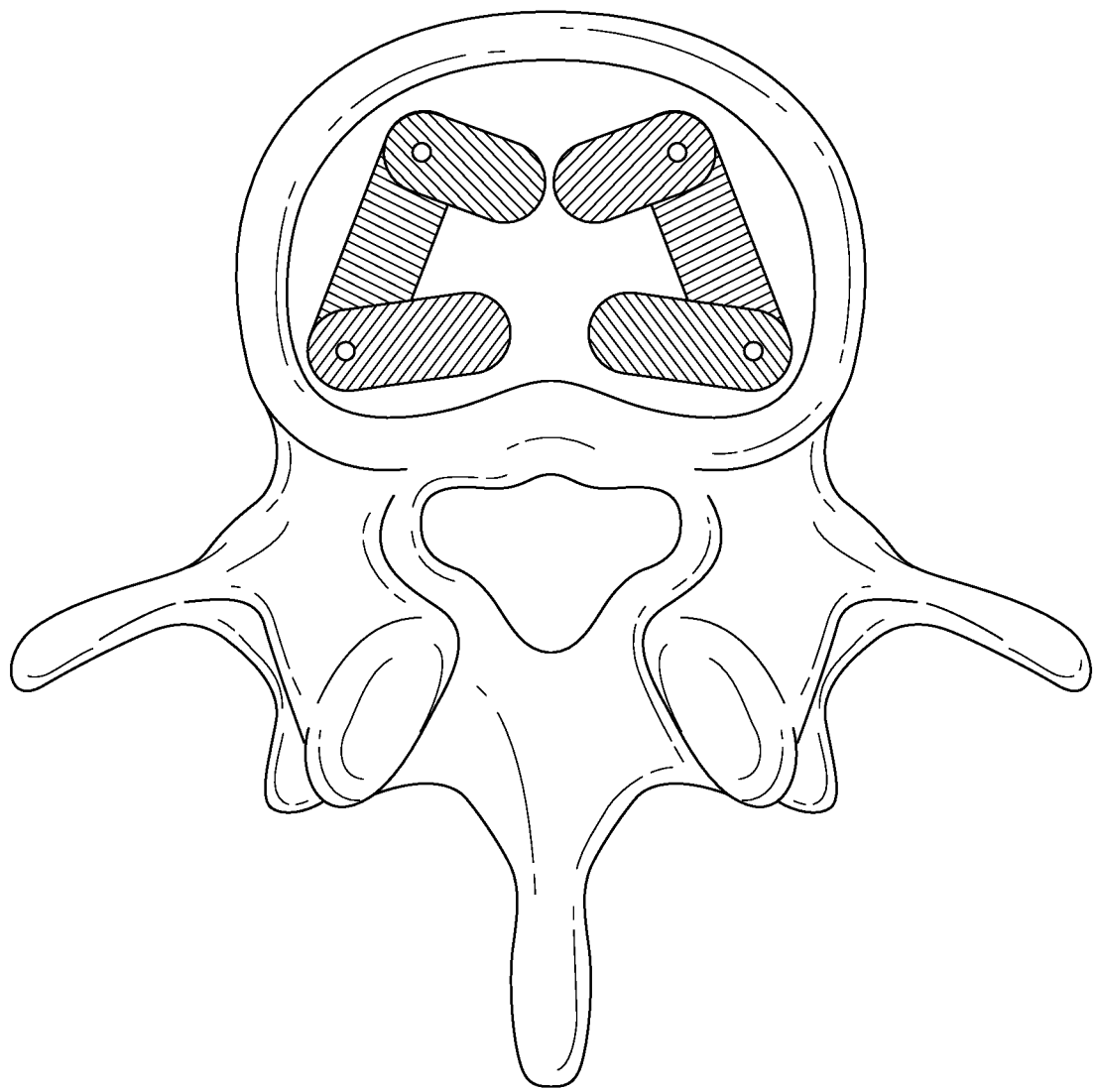
FIG. 9C depicts the hinge-mechanism embodiment from a top view within the vertebral space.

Another possible embodiment of the device may require a smaller incision to access the disc space. As shown in, for example, FIG. 9A-B, the device (9100) may, in aspects, have two or more elements with top and bottom plates with an elastic section in between that are connected via a hinge mechanism (9900). The implant is inserted through an incision and once placed in the disc space, the forward element of the device is rotated about the hinge so that it lies parallel to the back element (see, e.g., FIG. 9C).

Figure 10A:
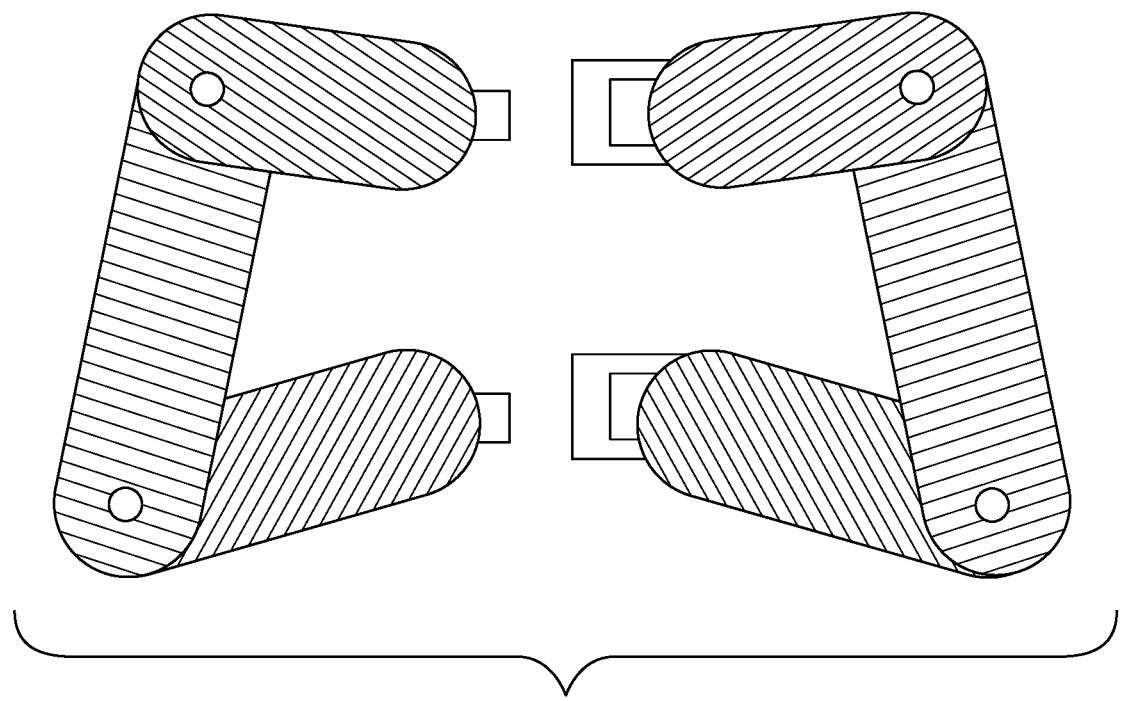
FIG. 10A depicts the multiple device hinge-mechanism embodiment from a top view.
Figure 10B:
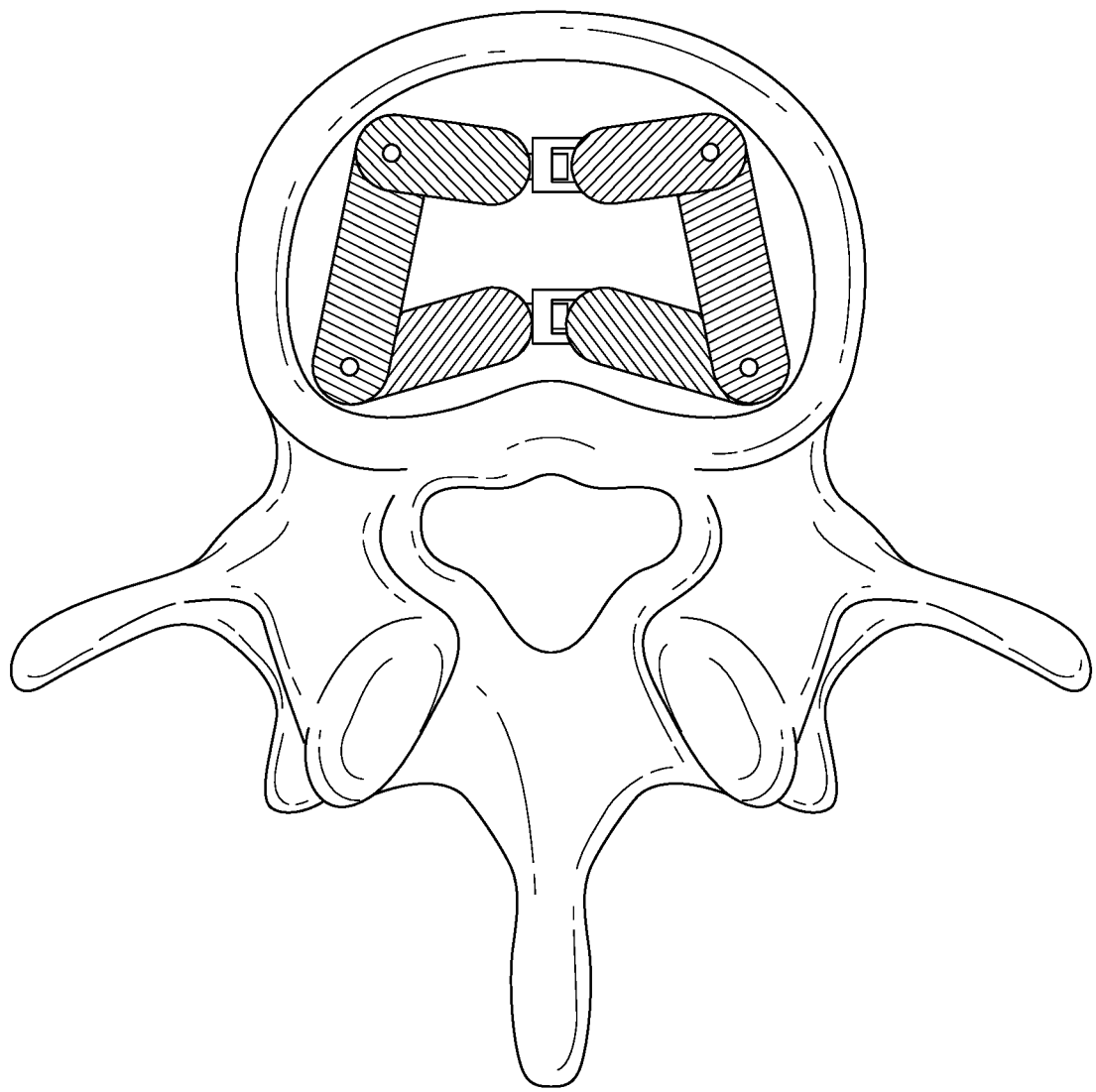
FIG. 10B depicts the multiple device hinge-mechanism embodiment from a top view within the vertebral space.

Such hinged elements may be scaled to a larger size so the one or more devices can be inserted into the disc space with one or more different polymer properties between the top and bottom plates. Such devices are depicted in FIG. 10A-B. The devices can be inserted in various orientations into the space as shown in FIG. 10B, particularly.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

A "vertebral element" includes a vertebrae, a vertebrae disc, a vertebrae above and below a disc, a space between vertebrae, a space in vertebrae, a vertebrae endplate, and/or a portion of a spinal column, alone or together in any combination.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A spinal intervertebral disc implant device for alignment and/or realignment of a spinal column in more than one plane or axis comprising an elastic polymer component, wherein the elastic polymer component is capable of:
   (a) absorbing shock;
   (b) applying asymmetric force(s) to a vertebrae or vertebral element and adjacent vertebrae or vertebral element from within an intervertebral disc space by extension and/or contraction of one or more portions of the elastic polymer component;
   (c) aligning and/or realigning a spinal column; and
   (d) responding to loading and/or movement of the spinal column, and
wherein a spring constant of the elastic polymer component remains steady after being implanted in or on the spinal column.

2. The spinal intervertebral disc implant device of claim 1, wherein the elastic polymer component comprises one or more polymer springs capable of applying force(s) to the adjacent vertebrae or vertebral element by extension or contraction of the one or more polymer springs to align and/or realign the spinal column and respond to loading and/or movement of the spinal column.

3. The spinal intervertebral disc implant device of claim 1, wherein the spinal intervertebral disc implant device further comprises a top face and a bottom face, wherein the elastic polymer component is continuous from the top face to the bottom face.

4. The spinal intervertebral disc implant device of claim 1, wherein the spinal intervertebral disc implant device is capable of being intraoperatively wedged and inserted in a space between two vertebrae resulting in the spinal intervertebral disc implant device being higher on a concave-lateral side of the spinal column and lower on a convex-lateral side of the spinal column.

5. The spinal intervertebral disc implant device of claim 1, wherein the elastic polymer component, when the spinal intervertebral disc implant device is implanted in or on the spinal column, elastically expands on a concave-lateral side of the spinal column and elastically compresses on a convex-lateral side of the spinal column, wherein the elastic properties of the spinal intervertebral disc implant device force a vertebrae into a different alignment.

6. The spinal intervertebral disc implant device of claim 1, wherein the spinal intervertebral disc implant device comprises a shape or form that resembles or is similar in shape to a vertebral disc.

7. The spinal intervertebral disc implant device of claim 1, further comprising external facing ridges, spikes, bumps, and/or protrusions capable of increasing a surface area between the spinal intervertebral disc implant device and a vertebrae or vertebral element, wherein the increased surface area is capable of causing complete or partial frictional fixation.

8. The spinal intervertebral disc implant device of claim 1, wherein the elasticity of the spinal intervertebral disc implant device is configured to apply force(s) which propagate through all or part of the spinal column to align or re-align a vertebrae or vertebral element adjacent to a vertebrae or vertebral element contacting the spinal intervertebral disc implant device.

9. The spinal intervertebral disc implant device of claim 1, wherein the elastic polymer component is configured to be preoperatively wedged and inserted in a space between two vertebrae, wherein the elastic polymer component is higher on a side meant to be implanted in a concave-lateral side of the spinal column and lower on a side meant to be implanted in a convex-lateral side of the spinal column.

10. The spinal intervertebral disc implant device of claim 1, further comprising one or more regions within the elastic polymer component having elasticity that resembles or is similar in elastic properties to a vertebral disc or portions of a vertebral disc.

11. The spinal intervertebral disc implant device of claim 1, wherein the elastic polymer component comprises multiple sections capable of having differing heights or differing elastic properties.

12. The spinal intervertebral disc implant device of claim 1, further comprising springs in or around the elastic polymer component.

13. The spinal intervertebral disc implant device of claim 1, wherein the spinal intervertebral disc implant device comprises a plurality of separate sections inserted in a space between two vertebrae on more than one side of the spinal column, wherein a shape or form of one or more of the separate sections resemble or are similar in shape to a vertebral disc or portion of a vertebral disc.

14. The spinal intervertebral disc implant device of claim 13, wherein the plurality of separate sections are connected by one or more of a dowel-to-hole connection, a hook connection, a magnetic connection, and/or a screw connection.

15. A method of treating spinal deformity comprising implanting an elastic device configured to be inserted between two spinal vertebrae, wherein a spring constant of the elastic device remains steady after being inserted between the two spinal vertebrae, wherein the elastic device is further capable of applying asymmetric forces to adjacent vertebrae to realign a vertebrae, vertebral element, and/or spinal column, wherein the asymmetric forces propagate through all or part of a spinal column in which the elastic device is implanted, and wherein the elastic device is capable of treating the vertebrae, vertebral element, and/or spinal column in both the sagittal and coronal planes within the cervical, thoracic, or lumbar vertebrae.

16. The method of claim 15, wherein the elastic device is positioned between adjacent vertebrae at an apex of curvature, wherein the elastic device increases a height of a disc space on a concave side of the spinal column and decreases a height of a disc space on a convex side of the spinal column by applying forces to an endplate of an adjacent vertebrae or vertebral element over time.

17. The method of claim 15, wherein the elastic device is capable of attaching to endplates of adjacent vertebrae by a screw fixation system, wherein one or more screws are inserted through threads in either a top or bottom face of the elastic device, or both faces of the elastic device, and into the endplates.

18. The method of claim 17, wherein the screws are inserted through a protrusion of the elastic device parallel to a vertical face of a vertebrae.

* * * * *